US008360629B2

(12) United States Patent
Globerman et al.

(10) Patent No.: US 8,360,629 B2
(45) Date of Patent: Jan. 29, 2013

(54) MIXING APPARATUS HAVING CENTRAL AND PLANETARY MIXING ELEMENTS

(75) Inventors: Oren Globerman, Kfar-Shmaryahu (IL); Mordechay Beyar, Caesarea (IL)

(73) Assignee: DePuy Spine, Inc., Raynham, MA (US)

( * ) Notice: Subject to any disclaimer, the term of this patent is extended or adjusted under 35 U.S.C. 154(b) by 908 days.

(21) Appl. No.: 11/428,908

(22) Filed: Jul. 6, 2006

(65) Prior Publication Data

US 2008/0212405 A1    Sep. 4, 2008

Related U.S. Application Data

(63) Continuation-in-part of application No. 11/360,251, filed on Feb. 22, 2006.

(60) Provisional application No. 60/738,556, filed on Nov. 22, 2005, provisional application No. 60/762,789, filed on Jan. 26, 2006, provisional application No. 60/765,484, filed on Feb. 2, 2006.

(51) Int. Cl.
*B01F 7/30* (2006.01)

(52) U.S. Cl. .................... 366/288; 366/245; 366/309

(58) Field of Classification Search ............ 366/64–67, 366/96–98, 139, 288, 241–252, 272, 309–313
See application file for complete search history.

(56) References Cited

U.S. PATENT DOCUMENTS

| 229,932 | A | * | 7/1880 | Witsil | ............ 209/465 |
| 370,335 | A | * | 9/1887 | Hunter | ............ 366/288 |
| 817,973 | A | | 4/1906 | Hausman | |
| 833,044 | A | | 10/1906 | Goodhugh | |
| 843,587 | A | | 2/1907 | DePew | |
| 1,175,530 | A | | 3/1916 | Kirchoff | |
| 1,612,281 | A | * | 12/1926 | Goetz | ............ 366/244 |
| 1,612,996 | A | | 1/1927 | Waagbo | |
| 1,733,516 | A | * | 10/1929 | Jamieson et al. | ............ 366/300 |
| 1,894,274 | A | | 1/1933 | Jacques | |
| 2,067,458 | A | | 1/1937 | Nichols | |
| 2,123,712 | A | | 7/1938 | Clark | |
| 2,283,915 | A | | 5/1942 | Cole | |
| 2,394,488 | A | | 2/1946 | Rotter et al. | |
| 2,425,867 | A | | 8/1947 | Davis | |
| 2,435,647 | A | | 2/1948 | Engseth | |
| 2,497,762 | A | | 2/1950 | Davis | |
| 2,521,569 | A | | 9/1950 | Davis | |
| 2,567,960 | A | | 9/1951 | Meyers et al. | |
| 2,745,575 | A | | 5/1956 | Spencer | |
| 2,773,500 | A | | 12/1956 | Young | |
| 2,808,239 | A | * | 10/1957 | Reiffen | ............ 366/94 |
| 2,874,877 | A | | 2/1959 | Spencer | |
| 2,918,841 | A | | 12/1959 | Poupitch | |

(Continued)

FOREIGN PATENT DOCUMENTS

| AU | 724544 | 11/1996 |
| AU | 9865136 | 9/1998 |

(Continued)

OTHER PUBLICATIONS

International Search Report, from corresponding PCT/IL07/00833, dated Apr. 4, 2008.

(Continued)

*Primary Examiner* — Charles E Cooley
(74) *Attorney, Agent, or Firm* — Nutter McClennen & Fish LLP

(57) ABSTRACT

A mixing apparatus comprising: a) a mixing well characterized by an internal volume not exceeding 100 ml.; b) a drive mechanism including a stationary circumferential gear on an inner surface of the mixing well; and c) a planetary mixing element driven by a mixing element gear which engages the stationary circumferential gear.

22 Claims, 10 Drawing Sheets

U.S. PATENT DOCUMENTS

| | | | |
|---|---|---|---|
| 2,928,574 A | 3/1960 | Wagner | |
| 2,970,773 A | 2/1961 | Horace et al. | |
| 3,058,413 A | 11/1962 | Cavalieri | |
| 3,063,449 A | 11/1962 | Schultz | |
| 3,075,746 A * | 1/1963 | Yablonski et al. | 366/288 |
| 3,108,593 A | 10/1963 | Glassman | |
| 3,151,847 A * | 10/1964 | Broomall | 416/111 |
| 3,198,194 A | 8/1965 | Wilburn | |
| 3,216,616 A | 11/1965 | Blankenship, Jr. | |
| 3,224,744 A * | 12/1965 | Broomall | 366/288 |
| 3,225,760 A | 12/1965 | Di Cosola | |
| 3,254,494 A | 6/1966 | Chartouni | |
| 3,381,566 A | 5/1968 | Passer | |
| 3,426,364 A | 2/1969 | Lumb | |
| 3,515,873 A | 6/1970 | Higgins | |
| 3,568,885 A | 3/1971 | Spencer | |
| 3,572,556 A | 3/1971 | Pogacar | |
| 3,615,240 A | 10/1971 | Sanz | |
| 3,674,011 A | 7/1972 | Michel et al. | |
| 3,701,350 A | 10/1972 | Guenther | |
| 3,750,667 A | 8/1973 | Pshenichny et al. | |
| 3,789,727 A | 2/1974 | Moran | |
| 3,796,303 A | 3/1974 | Allet-Coche | |
| 3,798,982 A | 3/1974 | Lundquist | |
| 3,846,846 A | 11/1974 | Fischer | |
| 3,850,158 A | 11/1974 | Elias et al. | |
| 3,867,728 A | 2/1975 | Stubstad et al. | |
| 3,873,008 A | 3/1975 | Jahn | |
| 3,875,595 A | 4/1975 | Froning | |
| 3,896,504 A | 7/1975 | Fischer | |
| 3,901,408 A | 8/1975 | Boden et al. | |
| 3,921,858 A | 11/1975 | Bemm | |
| 3,931,914 A | 1/1976 | Hosaka et al. | |
| 3,942,407 A | 3/1976 | Mortensen | |
| 3,976,060 A | 8/1976 | Hildebrandt et al. | |
| 3,993,250 A | 11/1976 | Shure | |
| 4,011,602 A | 3/1977 | Rybicki et al. | |
| 4,077,494 A | 3/1978 | Spaude et al. | |
| 4,079,917 A * | 3/1978 | Popeil | 366/244 |
| 4,090,640 A | 5/1978 | Smith et al. | |
| 4,093,576 A | 6/1978 | Dwijn | |
| 4,105,145 A | 8/1978 | Capra | |
| 4,115,346 A | 9/1978 | Gross et al. | |
| 4,146,334 A | 3/1979 | Farrell | |
| 4,168,787 A | 9/1979 | Stamper | |
| 4,170,990 A | 10/1979 | Baumgart et al. | |
| 4,185,072 A | 1/1980 | Puderbaugh et al. | |
| 4,189,065 A | 2/1980 | Herold | |
| 4,198,975 A | 4/1980 | Haller | |
| 4,204,531 A | 5/1980 | Aginsky | |
| 4,239,113 A | 12/1980 | Gross et al. | |
| 4,250,887 A | 2/1981 | Dardik et al. | |
| 4,257,540 A | 3/1981 | Wegmann et al. | |
| 4,268,639 A | 5/1981 | Seidel et al. | |
| 4,274,163 A | 6/1981 | Malcom et al. | |
| 4,276,878 A | 7/1981 | Storz | |
| 4,277,184 A | 7/1981 | Solomon | |
| 4,298,144 A | 11/1981 | Pressi | |
| 4,309,777 A | 1/1982 | Patil | |
| 4,312,343 A | 1/1982 | LeVeen et al. | |
| 4,313,434 A | 2/1982 | Segal | |
| 4,326,567 A | 4/1982 | Mistarz | |
| 4,338,925 A | 7/1982 | Miller | |
| 4,341,691 A | 7/1982 | Anuta | |
| 4,346,708 A | 8/1982 | LeVeen et al. | |
| 4,349,921 A | 9/1982 | Kuntz | |
| 4,359,049 A | 11/1982 | Redl et al. | |
| 4,373,217 A | 2/1983 | Draenert | |
| 4,380,398 A * | 4/1983 | Burgess | 366/261 |
| 4,400,170 A | 8/1983 | McNaughton et al. | |
| 4,403,989 A | 9/1983 | Christensen et al. | |
| 4,404,327 A | 9/1983 | Crugnola et al. | |
| 4,405,249 A | 9/1983 | Scales | |
| 4,409,966 A | 10/1983 | Lambrecht et al. | |
| 4,453,539 A | 6/1984 | Raftopoulos et al. | |
| 4,474,572 A | 10/1984 | McNaughton et al. | |
| 4,475,856 A | 10/1984 | Toomingas | |
| 4,476,866 A | 10/1984 | Chin | |
| 4,487,602 A | 12/1984 | Christensen et al. | |
| 4,494,535 A | 1/1985 | Haig | |
| 4,500,658 A | 2/1985 | Fox | |
| 4,503,169 A | 3/1985 | Randklev | |
| 4,522,200 A | 6/1985 | Stednitz | |
| D279,499 S | 7/1985 | Case | |
| 4,543,966 A | 10/1985 | Islam et al. | |
| 4,546,767 A | 10/1985 | Smith | |
| 4,554,914 A | 11/1985 | Kapp et al. | |
| 4,558,693 A | 12/1985 | Lash et al. | |
| 4,562,598 A | 1/1986 | Kranz | |
| 4,576,152 A | 3/1986 | Muller et al. | |
| 4,588,583 A | 5/1986 | Pietsch et al. | |
| 4,593,685 A | 6/1986 | McKay et al. | |
| 4,595,006 A | 6/1986 | Burke et al. | |
| 4,600,118 A | 7/1986 | Martin | |
| 4,605,011 A | 8/1986 | Naslund | |
| 4,632,101 A | 12/1986 | Freedland | |
| 4,636,217 A | 1/1987 | Ogilvie et al. | |
| 4,642,099 A | 2/1987 | Phillips et al. | |
| 4,650,469 A | 3/1987 | Berg et al. | |
| 4,651,904 A | 3/1987 | Schuckmann | |
| 4,653,487 A | 3/1987 | Maale | |
| 4,653,489 A | 3/1987 | Tronzo et al. | |
| 4,664,298 A | 5/1987 | Shew | |
| 4,664,655 A | 5/1987 | Orentreich et al. | |
| 4,668,220 A | 5/1987 | Hawrylenko | |
| 4,668,295 A | 5/1987 | Abjpai | |
| 4,670,008 A | 6/1987 | Von Albertini | |
| 4,671,263 A | 6/1987 | Draenert | |
| 4,676,655 A | 6/1987 | Handler | |
| 4,676,781 A | 6/1987 | Phillips et al. | |
| 4,686,973 A | 8/1987 | Frisch | |
| 4,697,584 A | 10/1987 | Haynes | |
| 4,697,929 A * | 10/1987 | Muller | 366/97 |
| 4,704,035 A * | 11/1987 | Kowalczyk | 366/142 |
| 4,710,179 A | 12/1987 | Haber et al. | |
| 4,714,721 A | 12/1987 | Franek et al. | |
| 4,717,383 A | 1/1988 | Phillips et al. | |
| 4,718,910 A | 1/1988 | Draenert | |
| 4,722,948 A | 2/1988 | Sanderson | |
| 4,735,616 A | 4/1988 | Eibl et al. | |
| 4,737,151 A | 4/1988 | Clement et al. | |
| 4,747,832 A | 5/1988 | Buffet | |
| 4,758,096 A | 7/1988 | Gunnarsson | |
| 4,758,234 A | 7/1988 | Orentreich et al. | |
| 4,759,769 A | 7/1988 | Hedman et al. | |
| 4,762,515 A | 8/1988 | Grimm | |
| 4,767,033 A | 8/1988 | Gemperle | |
| 4,772,287 A | 9/1988 | Ray et al. | |
| 4,782,118 A | 11/1988 | Fontanille et al. | |
| 4,786,184 A * | 11/1988 | Berezkina et al. | 366/288 |
| 4,791,150 A | 12/1988 | Braden et al. | |
| 4,792,577 A | 12/1988 | Chen et al. | |
| 4,804,023 A | 2/1989 | Frearson | |
| 4,813,870 A | 3/1989 | Pitzen et al. | |
| 4,815,454 A | 3/1989 | Dozier | |
| 4,815,632 S | 3/1989 | Ball et al. | |
| 4,826,053 A | 5/1989 | Keller | |
| 4,830,227 A | 5/1989 | Ball et al. | |
| 4,837,279 A | 6/1989 | Arroyo | |
| 4,854,312 A | 8/1989 | Raftopoulos et al. | |
| 4,854,482 A | 8/1989 | Bergner | |
| 4,863,072 A | 9/1989 | Perler | |
| 4,869,906 A | 9/1989 | Dingeldein et al. | |
| 4,872,936 A | 10/1989 | Engelbrecht | |
| 4,892,231 A | 1/1990 | Ball | |
| 4,892,550 A | 1/1990 | Huebsch | |
| 4,902,649 A | 2/1990 | Kimura et al. | |
| 4,904,260 A | 2/1990 | Ray et al. | |
| 4,908,017 A | 3/1990 | Howson et al. | |
| 4,910,259 A | 3/1990 | Kindt-Larsen et al. | |
| 4,927,866 A | 5/1990 | Purrmann et al. | |
| 4,932,969 A | 6/1990 | Frey et al. | |
| 4,935,029 A | 6/1990 | Matsutani et al. | |
| 4,944,065 A | 7/1990 | Svanberg et al. | |
| 4,944,726 A | 7/1990 | Hilal et al. | |
| 4,946,077 A | 8/1990 | Olsen | |
| 4,946,285 A * | 8/1990 | Vennemeyer | 366/288 |

| Patent | | Date | Inventor |
|---|---|---|---|
| 4,946,901 | A | 8/1990 | Lechner et al. |
| 4,961,647 | A | 10/1990 | Coutts et al. |
| 4,966,601 | A | 10/1990 | Draenert |
| 4,968,303 | A | 11/1990 | Clarke et al. |
| 4,969,888 | A | 11/1990 | Scholten et al. |
| 4,973,301 | A | 11/1990 | Nissenkorn |
| 4,973,334 | A | 11/1990 | Ziemann |
| 4,978,336 | A | 12/1990 | Capozzi et al. |
| 4,983,164 | A | 1/1991 | Hook et al. |
| 4,994,065 | A | 2/1991 | Gibbs et al. |
| 4,995,868 | A | 2/1991 | Brazier |
| 5,004,501 | A | 4/1991 | Faccioli et al. |
| 5,006,112 | A | 4/1991 | Metzner |
| 5,012,066 | A | 4/1991 | Matsutani et al. |
| 5,012,413 | A | 4/1991 | Sroka et al. |
| 5,015,233 | A | 5/1991 | McGough et al. |
| 5,018,919 | A | 5/1991 | Stephan |
| 5,022,563 | A | 6/1991 | Marchitto et al. |
| 5,024,232 | A | 6/1991 | Smid et al. |
| 5,028,141 | A * | 7/1991 | Stiegelmann ............. 366/245 |
| 5,037,473 | A | 8/1991 | Antonucci et al. |
| 5,049,157 | A | 9/1991 | Mittelmeier et al. |
| 5,051,482 | A | 9/1991 | Tepic |
| 5,059,193 | A | 10/1991 | Kuslich |
| 5,059,199 | A | 10/1991 | Okada et al. |
| 5,061,128 | A | 10/1991 | Jahr et al. |
| 5,071,040 | A | 12/1991 | Laptewicz, Jr. |
| 5,074,871 | A | 12/1991 | Groshong |
| 5,078,919 | A | 1/1992 | Ashley et al. |
| 5,092,888 | A | 3/1992 | Iwamoto et al. |
| 5,102,413 | A | 4/1992 | Poddar |
| 5,108,403 | A | 4/1992 | Stern |
| 5,108,404 | A | 4/1992 | Scholten et al. |
| 5,112,333 | A | 5/1992 | Fixel |
| 5,114,240 | A | 5/1992 | Kindt-Larsen et al. |
| 5,116,335 | A | 5/1992 | Hannon |
| 5,122,400 | A | 6/1992 | Stewart |
| 5,123,926 | A | 6/1992 | Pisharodi |
| 5,125,971 | A | 6/1992 | Nonami et al. |
| 5,131,382 | A | 7/1992 | Meyer |
| 5,141,496 | A | 8/1992 | Dalto et al. |
| 5,145,250 | A | 9/1992 | Planck et al. |
| 5,147,903 | A | 9/1992 | Podszun et al. |
| 5,171,248 | A | 12/1992 | Ellis |
| 5,171,278 | A | 12/1992 | Pisharodi |
| 5,181,918 | A | 1/1993 | Brandhorst et al. |
| 5,188,259 | A | 2/1993 | Petit |
| 5,190,191 | A | 3/1993 | Reyman |
| 5,192,327 | A | 3/1993 | Brantigan |
| 5,193,907 | A | 3/1993 | Faccioli et al. |
| 5,209,753 | A | 5/1993 | Biedermann et al. |
| 5,217,147 | A | 6/1993 | Kaufman |
| 5,219,897 | A | 6/1993 | Murray |
| 5,236,445 | A | 8/1993 | Hayhurst et al. |
| 5,242,983 | A | 9/1993 | Kennedy et al. |
| 5,252,301 | A | 10/1993 | Nilson et al. |
| 5,254,092 | A | 10/1993 | Polyak |
| 5,258,420 | A | 11/1993 | Posey-Dowty et al. |
| 5,264,215 | A | 11/1993 | Nakabayashi et al. |
| 5,268,001 | A | 12/1993 | Nicholson et al. |
| 5,269,762 | A | 12/1993 | Armbruster et al. |
| 5,275,214 | A | 1/1994 | Rehberger |
| 5,276,070 | A | 1/1994 | Arroyo |
| 5,277,339 | A | 1/1994 | Shew et al. |
| 5,279,555 | A | 1/1994 | Lifshey |
| 5,290,260 | A | 3/1994 | Stines |
| 5,295,980 | A | 3/1994 | Ersek |
| 5,302,020 | A | 4/1994 | Kruse |
| 5,303,718 | A | 4/1994 | Krajicek |
| 5,304,147 | A | 4/1994 | Johnson et al. |
| 5,328,262 | A | 7/1994 | Lidgren et al. |
| 5,328,362 | A | 7/1994 | Watson et al. |
| 5,331,972 | A | 7/1994 | Wadhwani et al. |
| 5,333,951 | A | 8/1994 | Wakoh |
| 5,334,184 | A | 8/1994 | Bimman |
| 5,334,626 | A | 8/1994 | Lin |
| 5,336,699 | A | 8/1994 | Cooke et al. |
| 5,336,700 | A | 8/1994 | Murray |
| 5,344,232 | A | 9/1994 | Nelson et al. |
| 5,348,391 | A * | 9/1994 | Murray ............. 366/139 |
| 5,348,548 | A | 9/1994 | Meyer et al. |
| 5,350,372 | A | 9/1994 | Ikeda et al. |
| 5,354,287 | A | 10/1994 | Wacks |
| 5,356,382 | A | 10/1994 | Picha et al. |
| 5,368,046 | A | 11/1994 | Scarfone et al. |
| 5,368,386 | A * | 11/1994 | Murray ............. 366/139 |
| 5,370,221 | A | 12/1994 | Magnusson et al. |
| 5,372,583 | A | 12/1994 | Roberts et al. |
| 5,374,427 | A | 12/1994 | Stille et al. |
| 5,375,583 | A | 12/1994 | Meyer et al. |
| 5,376,123 | A | 12/1994 | Klaue et al. |
| 5,380,772 | A | 1/1995 | Hasegawa et al. |
| 5,385,081 | A | 1/1995 | Sneddon |
| 5,385,566 | A | 1/1995 | Ullmark |
| 5,387,191 | A | 2/1995 | Hemstreet et al. |
| 5,390,683 | A | 2/1995 | Pisharodi |
| 5,395,167 | A * | 3/1995 | Murray ............. 366/139 |
| 5,395,326 | A | 3/1995 | Haber et al. |
| 5,398,483 | A | 3/1995 | Smith et al. |
| 5,401,806 | A | 3/1995 | Braden et al. |
| 5,411,180 | A | 5/1995 | Dumelle |
| 5,415,474 | A | 5/1995 | Nelson et al. |
| 5,423,850 | A | 6/1995 | Berger |
| 5,431,654 | A | 7/1995 | Nic |
| 5,435,645 | A | 7/1995 | Faccioli et al. |
| 5,443,182 | A | 8/1995 | Tanaka et al. |
| 5,445,639 | A | 8/1995 | Kuslich et al. |
| 5,450,924 | A | 9/1995 | Tseng |
| 5,454,365 | A | 10/1995 | Bonutti |
| 5,456,267 | A | 10/1995 | Stark |
| 5,468,245 | A | 11/1995 | Vargas, III |
| 5,480,400 | A | 1/1996 | Berger |
| 5,480,403 | A | 1/1996 | Lee |
| 5,482,187 | A | 1/1996 | Poulsen et al. |
| 5,492,247 | A | 2/1996 | Shu et al. |
| 5,494,349 | A * | 2/1996 | Seddon ............. 366/139 |
| 5,501,374 | A | 3/1996 | Laufer et al. |
| 5,501,520 | A | 3/1996 | Lidgren et al. |
| 5,501,695 | A | 3/1996 | Anspach, Jr. et al. |
| 5,512,610 | A | 4/1996 | Lin |
| 5,514,135 | A | 5/1996 | Earle |
| 5,514,137 | A | 5/1996 | Coutts |
| 5,518,498 | A | 5/1996 | Lindenberg et al. |
| 5,520,690 | A | 5/1996 | Errico et al. |
| 5,522,816 | A | 6/1996 | Dinello et al. |
| 5,522,899 | A | 6/1996 | Michelson |
| 5,526,853 | A | 6/1996 | McPhee et al. |
| 5,534,028 | A | 7/1996 | Bao et al. |
| 5,536,262 | A | 7/1996 | Velasquez |
| 5,545,460 | A | 8/1996 | Tanaka et al. |
| 5,548,001 | A | 8/1996 | Podszun et al. |
| 5,549,380 | A | 8/1996 | Lidgren et al. |
| 5,549,381 | A | 8/1996 | Hays et al. |
| 5,549,679 | A | 8/1996 | Kuslich |
| 5,551,778 | A | 9/1996 | Hauke et al. |
| 5,554,101 | A | 9/1996 | Matula et al. |
| 5,556,201 | A * | 9/1996 | Veltrop et al. ............. 366/203 |
| 5,558,136 | A | 9/1996 | Orrico |
| 5,558,639 | A | 9/1996 | Gangemi et al. |
| 5,571,189 | A | 11/1996 | Kuslich |
| 5,573,265 | A | 11/1996 | Pradel |
| 5,578,035 | A | 11/1996 | Lin |
| 5,586,821 | A | 12/1996 | Bonitati et al. |
| 5,588,745 | A | 12/1996 | Tanaka et al. |
| 5,591,197 | A | 1/1997 | Orth et al. |
| 5,601,557 | A | 2/1997 | Hayhurst |
| 5,603,701 | A | 2/1997 | Fisher |
| 5,609,637 | A | 3/1997 | Biedermann et al. |
| 5,624,184 | A | 4/1997 | Chan |
| 5,630,806 | A | 5/1997 | Inagaki et al. |
| 5,634,880 | A | 6/1997 | Feldman et al. |
| 5,637,097 | A | 6/1997 | Yoon |
| 5,638,997 | A | 6/1997 | Hawkins et al. |
| 5,641,010 | A | 6/1997 | Maier |
| 5,645,598 | A | 7/1997 | Brosnahan, III |
| 5,647,856 | A | 7/1997 | Eykmann |
| 5,653,686 | A | 8/1997 | Coulter et al. |
| 5,658,310 | A | 8/1997 | Berger |

| | | | | | | |
|---|---|---|---|---|---|---|
| 5,660,186 A | 8/1997 | Bachir | | 6,039,761 A | 3/2000 | Li et al. |
| 5,665,067 A | 9/1997 | Linder et al. | | 6,040,408 A | 3/2000 | Koole |
| 5,681,317 A | 10/1997 | Caldarise | | 6,041,977 A | 3/2000 | Lisi |
| 5,683,451 A | 11/1997 | Lenker et al. | | 6,042,262 A | 3/2000 | Hajianpour |
| 5,685,826 A | 11/1997 | Bonutti | | 6,045,555 A | 4/2000 | Smith et al. |
| 5,690,606 A | 11/1997 | Slotman | | 6,048,346 A | 4/2000 | Reiley |
| 5,693,100 A | 12/1997 | Pisharodi | | 6,049,026 A | 4/2000 | Muschler |
| 5,697,977 A | 12/1997 | Pisharodi | | 6,075,067 A | 6/2000 | Lidgren |
| 5,698,611 A | 12/1997 | Okada et al. | | 6,080,579 A | 6/2000 | Hanley, Jr. |
| 5,702,448 A | 12/1997 | Buechel et al. | | 6,080,801 A | 6/2000 | Draenert et al. |
| 5,704,895 A | 1/1998 | Scott et al. | | 6,080,811 A | 6/2000 | Schehlmann et al. |
| 5,707,390 A | 1/1998 | Bonutti | | 6,083,229 A | 7/2000 | Constantz et al. |
| 5,718,707 A | 2/1998 | Mikhail | | 6,086,594 A | 7/2000 | Brown |
| 5,720,753 A | 2/1998 | Sander et al. | | 6,103,779 A | 8/2000 | Guzauskas |
| 5,725,341 A | 3/1998 | Hofmeister | | 6,116,773 A | 9/2000 | Murray |
| 5,725,529 A | 3/1998 | Nicholson et al. | | 6,120,174 A | 9/2000 | Hoag et al. |
| 5,747,553 A | 5/1998 | Guzauskas | | 6,124,373 A | 9/2000 | Peter et al. |
| 5,752,935 A | 5/1998 | Robinson et al. | | 6,126,689 A | 10/2000 | Brett |
| 5,752,969 A | 5/1998 | Cunci et al. | | 6,127,597 A | 10/2000 | Beyar et al. |
| 5,752,974 A | 5/1998 | Rhee | | 6,129,763 A | 10/2000 | Chauvin et al. |
| 5,755,732 A | 5/1998 | Green et al. | | 6,132,396 A | 10/2000 | Antanavich et al. |
| 5,759,186 A | 6/1998 | Bachmann et al. | | 6,136,038 A | 10/2000 | Raab |
| 5,763,092 A | 6/1998 | Lee et al. | | 6,139,509 A | 10/2000 | Yuan et al. |
| 5,779,356 A | 7/1998 | Chan | | 6,142,998 A | 11/2000 | Smith et al. |
| 5,782,713 A | 7/1998 | Yang | | 6,146,401 A | 11/2000 | Yoon et al. |
| 5,782,747 A | 7/1998 | Zimmon | | 6,149,651 A | 11/2000 | Drewry et al. |
| 5,782,830 A | 7/1998 | Farris | | 6,149,655 A | 11/2000 | Constantz et al. |
| 5,782,838 A | 7/1998 | Beyar et al. | | 6,149,664 A | 11/2000 | Kurz |
| 5,785,647 A | 7/1998 | Tompkins et al. | | 6,160,033 A | 12/2000 | Nies |
| 5,792,044 A | 8/1998 | Foley | | 6,161,955 A | 12/2000 | Rademaker |
| 5,795,922 A | 8/1998 | Demian et al. | | 6,168,597 B1 | 1/2001 | Biedermann et al. |
| 5,797,678 A * | 8/1998 | Murray .......... 366/139 | | 6,174,935 B1 | 1/2001 | Matsunae et al. |
| 5,800,169 A | 9/1998 | Muhlbauer | | 6,176,607 B1 | 1/2001 | Hajianpour |
| 5,800,409 A | 9/1998 | Bruce | | 6,183,441 B1 | 2/2001 | Kriesel et al. |
| 5,800,549 A | 9/1998 | Bao et al. | | 6,183,516 B1 | 2/2001 | Burkinshaw et al. |
| 5,800,550 A | 9/1998 | Sertich | | 6,187,015 B1 | 2/2001 | Brenneman |
| 5,820,321 A | 10/1998 | Gruber | | 6,190,381 B1 | 2/2001 | Olsen et al. |
| 5,824,087 A | 10/1998 | Aspden et al. | | 6,210,031 B1 | 4/2001 | Murray |
| 5,826,713 A | 10/1998 | Sunago et al. | | 6,214,012 B1 | 4/2001 | Karpman et al. |
| 5,826,753 A | 10/1998 | Fehlig et al. | | 6,214,016 B1 | 4/2001 | Williams et al. |
| 5,827,289 A | 10/1998 | Reiley et al. | | 6,214,037 B1 | 4/2001 | Mitchell et al. |
| 5,829,875 A | 11/1998 | Hagel et al. | | 6,217,566 B1 | 4/2001 | Ju et al. |
| 5,830,194 A | 11/1998 | Anwar et al. | | 6,217,581 B1 | 4/2001 | Tolson |
| 5,839,621 A | 11/1998 | Tada | | 6,217,608 B1 | 4/2001 | Penn et al. |
| 5,842,785 A * | 12/1998 | Brown et al. .......... 366/139 | | 6,221,029 B1 | 4/2001 | Mathis et al. |
| 5,865,802 A | 2/1999 | Yoon et al. | | 6,224,604 B1 | 5/2001 | Suddaby |
| 5,876,116 A | 3/1999 | Barker et al. | | 6,228,068 B1 | 5/2001 | Yoon |
| 5,876,457 A | 3/1999 | Picha et al. | | 6,228,082 B1 | 5/2001 | Baker et al. |
| 5,882,340 A | 3/1999 | Yoon | | 6,231,615 B1 | 5/2001 | Preissman |
| 5,884,818 A | 3/1999 | Campbell | | 6,235,043 B1 | 5/2001 | Reiley et al. |
| 5,893,488 A | 4/1999 | Hoag et al. | | 6,238,399 B1 | 5/2001 | Heller et al. |
| 5,893,850 A | 4/1999 | Cachia | | 6,241,734 B1 | 6/2001 | Scribner et al. |
| 5,902,839 A | 5/1999 | Lautenschlager et al. | | 6,245,101 B1 | 6/2001 | Drasler et al. |
| 5,911,721 A | 6/1999 | Nicholson et al. | | 6,248,110 B1 | 6/2001 | Reiley et al. |
| 5,918,702 A | 7/1999 | Cheng et al. | | 6,254,268 B1 | 7/2001 | Long |
| 5,918,770 A | 7/1999 | Camm et al. | | 6,261,289 B1 | 7/2001 | Levy |
| 5,925,051 A | 7/1999 | Mikhail | | 6,264,618 B1 | 7/2001 | Landi et al. |
| 5,928,239 A | 7/1999 | Mirza | | 6,264,659 B1 | 7/2001 | Ross et al. |
| 5,931,347 A | 8/1999 | Haubrich | | 6,264,660 B1 | 7/2001 | Schmidt et al. |
| 5,941,851 A | 8/1999 | Coffey et al. | | 6,273,916 B1 | 8/2001 | Murphy |
| 5,954,671 A | 9/1999 | O'Neill | | 6,281,271 B1 | 8/2001 | Rumphorst et al. |
| 5,954,728 A | 9/1999 | Heller et al. | | 6,309,395 B1 | 10/2001 | Smith et al. |
| 5,961,211 A | 10/1999 | Barker et al. | | 6,309,420 B1 | 10/2001 | Preissman |
| 5,968,008 A | 10/1999 | Grams | | 6,312,149 B1 | 11/2001 | Sjovall et al. |
| 5,968,044 A | 10/1999 | Nicholson et al. | | 6,325,812 B1 | 12/2001 | Dubrul et al. |
| 5,968,999 A | 10/1999 | Ramp et al. | | 6,348,055 B1 | 2/2002 | Preissman |
| 5,972,015 A | 10/1999 | Scribner et al. | | 6,348,518 B1 | 2/2002 | Montgomery |
| 5,980,527 A | 11/1999 | Cohen et al. | | 6,350,271 B1 | 2/2002 | Kurz et al. |
| 5,993,535 A | 11/1999 | Sawamura et al. | | 6,361,539 B1 | 3/2002 | Heller et al. |
| 5,997,544 A | 12/1999 | Nies et al. | | 6,367,962 B1 | 4/2002 | Mizutani et al. |
| 6,004,325 A | 12/1999 | Vargas, III | | 6,375,659 B1 | 4/2002 | Erbe et al. |
| 6,007,496 A | 12/1999 | Brannon | | 6,375,682 B1 | 4/2002 | Fleischmann et al. |
| 6,017,349 A | 1/2000 | Heller et al. | | 6,383,188 B2 | 5/2002 | Kuslich et al. |
| 6,019,765 A | 2/2000 | Thornhill et al. | | 6,383,190 B1 | 5/2002 | Preissman |
| 6,019,776 A | 2/2000 | Preissman et al. | | 6,395,007 B1 | 5/2002 | Bhatnagar |
| 6,019,789 A | 2/2000 | Dinh et al. | | 6,402,701 B1 | 6/2002 | Kaplan et al. |
| 6,020,396 A | 2/2000 | Jacobs | | 6,402,758 B1 | 6/2002 | Tolson |
| 6,033,105 A | 3/2000 | Barker et al. | | 6,406,175 B1 | 6/2002 | Marino |
| 6,033,411 A | 3/2000 | Preissman | | 6,409,972 B1 | 6/2002 | Chan |

| | | |
|---|---|---|
| 6,410,612 B1 | 6/2002 | Hatanaka |
| 6,425,887 B1 | 7/2002 | McGuckin et al. |
| 6,431,743 B1 | 8/2002 | Mizutani et al. |
| 6,433,037 B1 | 8/2002 | Guzauskas |
| 6,436,143 B1 | 8/2002 | Ross et al. |
| 6,439,439 B1 | 8/2002 | Rickard |
| 6,443,334 B1 | 9/2002 | John et al. |
| 6,447,478 B1 | 9/2002 | Maynards |
| 6,450,973 B1 | 9/2002 | Murphy |
| 6,458,117 B1 | 10/2002 | Pollins, Sr. |
| 6,479,565 B1 | 11/2002 | Stanley |
| 6,488,667 B1 | 12/2002 | Murphy |
| 6,500,182 B2 | 12/2002 | Foster |
| 6,502,608 B1 | 1/2003 | Burchett et al. |
| 6,527,144 B2 | 3/2003 | Ritsche et al. |
| 6,550,957 B2 | 4/2003 | Mizutani et al. |
| 6,554,833 B2 | 4/2003 | Levy et al. |
| 6,572,256 B2 | 6/2003 | Seaton et al. |
| 6,575,331 B1 | 6/2003 | Peeler et al. |
| 6,575,919 B1 | 6/2003 | Reiley et al. |
| 6,582,439 B1 | 6/2003 | Sproul |
| 6,592,559 B1 | 7/2003 | Pakter et al. |
| 6,599,293 B2 | 7/2003 | Tague et al. |
| 6,599,520 B2 | 7/2003 | Scarborough et al. |
| 6,613,018 B2 | 9/2003 | Bagga |
| 6,613,054 B2 | 9/2003 | Scribner et al. |
| 6,626,912 B2 | 9/2003 | Speitling |
| 6,641,587 B2 | 11/2003 | Scribner et al. |
| 6,645,213 B2 | 11/2003 | Sand et al. |
| 6,662,969 B2 | 12/2003 | Peeler et al. |
| 6,676,664 B1 | 1/2004 | Al-Assir |
| 6,689,823 B1 | 2/2004 | Bellare et al. |
| 6,702,455 B2 * | 3/2004 | Vendrely et al. ............ 366/130 |
| 6,712,853 B2 | 3/2004 | Kuslich |
| 6,716,216 B1 | 4/2004 | Boucher et al. |
| 6,719,761 B1 | 4/2004 | Reiley et al. |
| 6,720,417 B1 | 4/2004 | Walter |
| 6,730,095 B2 | 5/2004 | Olson, Jr. et al. |
| 6,752,180 B2 | 6/2004 | Delay |
| 6,758,837 B2 | 7/2004 | Peciat et al. |
| 6,759,449 B2 | 7/2004 | Kimura et al. |
| 6,767,973 B2 | 7/2004 | Suau et al. |
| 6,770,079 B2 | 8/2004 | Bhatnagar |
| 6,779,566 B2 | 8/2004 | Engel |
| 6,780,175 B1 | 8/2004 | Sachdeva et al. |
| 6,783,515 B1 | 8/2004 | Miller et al. |
| 6,787,584 B2 | 9/2004 | Jia et al. |
| 6,796,987 B2 | 9/2004 | Tague et al. |
| 6,852,439 B2 | 2/2005 | Frank |
| 6,874,927 B2 * | 4/2005 | Foster ............................ 366/139 |
| 6,875,219 B2 | 4/2005 | Arramon et al. |
| 6,887,246 B2 | 5/2005 | Bhatnagar |
| 6,916,308 B2 | 7/2005 | Dixon et al. |
| 6,957,747 B2 | 10/2005 | Peeler et al. |
| 6,974,247 B2 | 12/2005 | Frei et al. |
| 6,979,341 B2 | 12/2005 | Scribner et al. |
| 6,979,352 B2 | 12/2005 | Reynolds |
| 6,994,465 B2 | 2/2006 | Tague et al. |
| 6,997,930 B1 | 2/2006 | Jaggi |
| 7,008,433 B2 | 3/2006 | Voellmicke et al. |
| 7,025,771 B2 | 4/2006 | Kuslich et al. |
| 7,029,163 B2 | 4/2006 | Barker et al. |
| 7,044,954 B2 | 5/2006 | Reiley |
| 7,048,743 B2 | 5/2006 | Miller |
| 7,066,942 B2 | 6/2006 | Treace |
| 7,087,040 B2 | 8/2006 | McGuckin |
| 7,091,258 B2 | 8/2006 | Neubert et al. |
| 7,097,648 B1 | 8/2006 | Globerman et al. |
| 7,112,205 B2 | 9/2006 | Carrison |
| 7,116,121 B1 | 10/2006 | Holcombe et al. |
| 7,252,671 B2 | 8/2007 | Scribner |
| 7,270,667 B2 | 9/2007 | Faccioli |
| 7,278,778 B2 * | 10/2007 | Sand ............................. 366/139 |
| 7,326,203 B2 | 2/2008 | Papineau et al. |
| 7,456,024 B2 | 11/2008 | Dahm et al. |
| 7,572,263 B2 | 8/2009 | Preissman |
| 7,604,618 B2 | 10/2009 | Dixon et al. |
| 7,666,205 B2 | 2/2010 | Weikel et al. |
| 8,066,713 B2 | 11/2011 | DiMauro et al. |
| 2001/0012968 A1 | 8/2001 | Preissman |
| 2001/0034527 A1 | 10/2001 | Scribner et al. |
| 2002/0008122 A1 | 1/2002 | Ritsche et al. |
| 2002/0010471 A1 | 1/2002 | Wironen |
| 2002/0010472 A1 | 1/2002 | Kuslich et al. |
| 2002/0013553 A1 | 1/2002 | Pajunk |
| 2002/0049448 A1 | 4/2002 | Sand et al. |
| 2002/0049449 A1 | 4/2002 | Bhatnagar et al. |
| 2002/0058947 A1 | 5/2002 | Hochschuler et al. |
| 2002/0067658 A1 * | 6/2002 | Vendrely et al. ............... 366/139 |
| 2002/0068939 A1 | 6/2002 | Levy et al. |
| 2002/0068974 A1 | 6/2002 | Kuslich et al. |
| 2002/0068975 A1 | 6/2002 | Teitelbaum et al. |
| 2002/0072768 A1 | 6/2002 | Ginn |
| 2002/0099384 A1 | 7/2002 | Scribner et al. |
| 2002/0099385 A1 | 7/2002 | Ralph et al. |
| 2002/0118595 A1 | 8/2002 | Miller |
| 2002/0156483 A1 | 10/2002 | Voellmicke et al. |
| 2002/0161373 A1 | 10/2002 | Osorio et al. |
| 2002/0177866 A1 | 11/2002 | Weikel et al. |
| 2002/0188300 A1 | 12/2002 | Arramon |
| 2002/0191487 A1 | 12/2002 | Sand |
| 2003/0018339 A1 | 1/2003 | Higueras et al. |
| 2003/0031698 A1 | 2/2003 | Roeder et al. |
| 2003/0032929 A1 | 2/2003 | McGuckin et al. |
| 2003/0036763 A1 | 2/2003 | Bhatnagar et al. |
| 2003/0040718 A1 | 2/2003 | Kust et al. |
| 2003/0050644 A1 | 3/2003 | Boucher et al. |
| 2003/0050702 A1 | 3/2003 | Berger |
| 2003/0078589 A1 | 4/2003 | Preissman |
| 2003/0109883 A1 | 6/2003 | Matsuzaki et al. |
| 2003/0109884 A1 | 6/2003 | Tague et al. |
| 2003/0144742 A1 | 7/2003 | King et al. |
| 2003/0162864 A1 | 8/2003 | Pearson et al. |
| 2003/0174576 A1 | 9/2003 | Tague et al. |
| 2003/0181963 A1 | 9/2003 | Pellegrino et al. |
| 2003/0185093 A1 * | 10/2003 | Vendrely et al. ............... 366/139 |
| 2003/0220414 A1 | 11/2003 | Axen et al. |
| 2003/0225364 A1 | 12/2003 | Kraft et al. |
| 2003/0231545 A1 | 12/2003 | Seaton |
| 2004/0010263 A1 | 1/2004 | Boucher et al. |
| 2004/0029996 A1 | 2/2004 | Kuhn |
| 2004/0054377 A1 | 3/2004 | Foster et al. |
| 2004/0059283 A1 | 3/2004 | Kirwan et al. |
| 2004/0068264 A1 | 4/2004 | Treace |
| 2004/0073139 A1 | 4/2004 | Hirsch et al. |
| 2004/0092946 A1 | 5/2004 | Bagga et al. |
| 2004/0098015 A1 | 5/2004 | Weikel et al. |
| 2004/0106913 A1 | 6/2004 | Eidenschink et al. |
| 2004/0122438 A1 | 6/2004 | Abrams |
| 2004/0132859 A1 | 7/2004 | Puckett, Jr. et al. |
| 2004/0133124 A1 | 7/2004 | Bates et al. |
| 2004/0133211 A1 | 7/2004 | Raskin et al. |
| 2004/0138759 A1 | 7/2004 | Muller et al. |
| 2004/0157952 A1 | 8/2004 | Soffiati et al. |
| 2004/0157954 A1 | 8/2004 | Imai et al. |
| 2004/0167532 A1 | 8/2004 | Olson et al. |
| 2004/0167562 A1 | 8/2004 | Osorio |
| 2004/0167625 A1 | 8/2004 | Beyar et al. |
| 2004/0193171 A1 | 9/2004 | DiMauro |
| 2004/0215202 A1 | 10/2004 | Preissman |
| 2004/0220672 A1 | 11/2004 | Shadduck |
| 2004/0226479 A1 | 11/2004 | Lyles et al. |
| 2004/0229972 A1 | 11/2004 | Klee et al. |
| 2004/0230309 A1 | 11/2004 | DiMauro et al. |
| 2004/0236313 A1 | 11/2004 | Klein |
| 2004/0249015 A1 | 12/2004 | Jia et al. |
| 2004/0249347 A1 | 12/2004 | Miller et al. |
| 2004/0260303 A1 | 12/2004 | Carrison |
| 2004/0260304 A1 | 12/2004 | Faccioli et al. |
| 2004/0267154 A1 | 12/2004 | Sutton et al. |
| 2005/0014273 A1 | 1/2005 | Dahm |
| 2005/0015148 A1 | 1/2005 | Jansen et al. |
| 2005/0025622 A1 | 2/2005 | Djeridane et al. |
| 2005/0058717 A1 | 3/2005 | Yetlinler |
| 2005/0060023 A1 | 3/2005 | Mitchell et al. |
| 2005/0070912 A1 | 3/2005 | Voellmicke |
| 2005/0070914 A1 | 3/2005 | Constantz et al. |
| 2005/0070915 A1 | 3/2005 | Mazzuca |

| | | | | | | |
|---|---|---|---|---|---|---|
| 2005/0083782 A1* | 4/2005 | Gronau et al. ............... 366/310 | DE | 3443167 | | 6/1986 |
| 2005/0113762 A1 | 5/2005 | Kay et al. | DE | 8716073 | | 3/1988 |
| 2005/0143827 A1 | 6/2005 | Globerman et al. | DE | 3817101 | | 11/1989 |
| 2005/0154081 A1 | 7/2005 | Yin et al. | DE | 3730298 | | 2/1990 |
| 2005/0180806 A1 | 8/2005 | Green | DE | 4104092 | | 8/1991 |
| 2005/0203206 A1 | 9/2005 | Trieu | DE | 293485 | | 9/1991 |
| 2005/0209695 A1 | 9/2005 | de Vries et al. | DE | 4016135 | | 3/1992 |
| 2005/0216025 A1 | 9/2005 | Chern Lin et al. | DE | 4315757 | | 11/1994 |
| 2005/0256220 A1 | 11/2005 | Lavergne et al. | DE | 19612276 | | 10/1997 |
| 2005/0281132 A1 | 12/2005 | Armstrong et al. | DE | 10258140 | | 7/2004 |
| 2006/0035997 A1 | 2/2006 | Orlowski et al. | EP | 20207 | | 6/1908 |
| 2006/0041033 A1 | 2/2006 | Bisig et al. | EP | 486638 | | 6/1938 |
| 2006/0052794 A1 | 3/2006 | McGill | EP | 0044877 | | 2/1982 |
| 2006/0074433 A1 | 4/2006 | McGill et al. | EP | 0190504 | | 3/1986 |
| 2006/0079905 A1 | 4/2006 | Beyar et al. | EP | 0177781 | | 4/1986 |
| 2006/0116643 A1 | 6/2006 | Dixon et al. | EP | 0235905 | | 9/1987 |
| 2006/0116689 A1 | 6/2006 | Albans et al. | EP | 0301759 | | 7/1988 |
| 2006/0116690 A1 | 6/2006 | Pagano | EP | 0242672 | | 9/1989 |
| 2006/0148923 A1 | 7/2006 | Ashman et al. | EP | 0425200 | | 10/1990 |
| 2006/0167148 A1 | 7/2006 | Engquist et al. | EP | 0423916 | | 4/1991 |
| 2006/0235338 A1 | 10/2006 | Pacheco | EP | 0475077 | | 3/1992 |
| 2006/0241644 A1 | 10/2006 | Osorio et al. | EP | 0511868 | | 4/1992 |
| 2006/0264695 A1 | 11/2006 | Viole et al. | EP | 0493789 | | 7/1992 |
| 2006/0264967 A1 | 11/2006 | Ferreyro et al. | EP | 0581387 | | 2/1994 |
| 2006/0266372 A1 | 11/2006 | Miller et al. | EP | 0614653 | | 9/1994 |
| 2006/0271061 A1 | 11/2006 | Beyar et al. | EP | 0669100 | | 8/1995 |
| 2006/0276819 A1 | 12/2006 | Osorio et al. | EP | 0748615 | | 12/1996 |
| 2007/0027230 A1 | 2/2007 | Beyar et al. | EP | 0763348 | | 3/1997 |
| 2007/0032567 A1 | 2/2007 | Beyar et al. | EP | 1074231 | | 2/2001 |
| 2007/0055266 A1 | 3/2007 | Osorio et al. | EP | 1095667 | | 5/2001 |
| 2007/0055267 A1 | 3/2007 | Osorio et al. | EP | 1103237 | | 5/2001 |
| 2007/0055278 A1 | 3/2007 | Osorio et al. | EP | 1104260 | | 6/2001 |
| 2007/0055280 A1 | 3/2007 | Osorio et al. | EP | 1464292 | | 10/2004 |
| 2007/0055284 A1 | 3/2007 | Osorio et al. | EP | 1148850 | | 4/2005 |
| 2007/0055285 A1 | 3/2007 | Osorio | EP | 1552797 | | 7/2005 |
| 2007/0055300 A1 | 3/2007 | Osorio et al. | EP | 1570873 | | 9/2005 |
| 2007/0060941 A1 | 3/2007 | Reiley et al. | EP | 1598 015 | | 11/2005 |
| 2007/0118142 A1 | 5/2007 | Krueger | EP | 1148851 | | 5/2006 |
| 2007/0142842 A1 | 6/2007 | Krueger et al. | EP | 1829518 | | 9/2007 |
| 2007/0197935 A1 | 8/2007 | Reiley et al. | EP | 1886647 | | 2/2008 |
| 2007/0198013 A1 | 8/2007 | Foley et al. | FR | 1548575 | | 10/1968 |
| 2007/0198023 A1 | 8/2007 | Sand et al. | FR | 2606282 | | 5/1988 |
| 2007/0198024 A1 | 8/2007 | Plishka et al. | FR | 2629337 | | 10/1989 |
| 2007/0282443 A1 | 12/2007 | Globerman et al. | FR | 2638972 | | 5/1990 |
| 2008/0039856 A1 | 2/2008 | DiMauro | FR | 2674119 | | 9/1992 |
| 2008/0044374 A1 | 2/2008 | Lavergne et al. | FR | 2690332 | | 10/1993 |
| 2008/0058827 A1 | 3/2008 | Osorio et al. | FR | 2712486 | | 5/1995 |
| 2008/0065087 A1 | 3/2008 | Osorio et al. | FR | 2722679 | | 1/1996 |
| 2008/0065089 A1 | 3/2008 | Osorio et al. | GB | 179502045 | | 4/1795 |
| 2008/0065137 A1 | 3/2008 | Boucher et al. | GB | 8331 | | 3/1904 |
| 2008/0065142 A1 | 3/2008 | Reiley et al. | GB | 408668 | | 4/1934 |
| 2008/0065190 A1 | 3/2008 | Osorio et al. | GB | 2114005 | | 8/1983 |
| 2008/0071283 A1 | 3/2008 | Osorio et al. | GB | 2156824 | | 10/1985 |
| 2008/0086133 A1 | 4/2008 | Kuslich et al. | GB | 2197691 | | 5/1988 |
| 2008/0132935 A1 | 6/2008 | Osorio et al. | GB | 2276560 | | 6/1993 |
| 2008/0140079 A1 | 6/2008 | Osorio et al. | GB | 2268068 | | 1/1994 |
| 2008/0140084 A1 | 6/2008 | Osorio et al. | GB | 2276560 A | * | 10/1994 |
| 2008/0200915 A1 | 8/2008 | Globerman et al. | GB | 2411849 | | 9/2005 |
| 2008/0212405 A1* | 9/2008 | Globerman et al. ......... 366/288 | GB | 2413280 | | 10/2005 |
| 2008/0228192 A1 | 9/2008 | Beyar et al. | GB | 2469749 A | * | 10/2010 |
| 2009/0264892 A1 | 10/2009 | Beyar et al. | JP | 54-009110 | | 1/1979 |
| 2009/0264942 A1 | 10/2009 | Beyar et al. | JP | 55-009242 U | | 1/1980 |
| 2009/0270872 A1 | 10/2009 | DiMauro | JP | 55-109440 | | 8/1980 |
| 2010/0065154 A1 | 3/2010 | Globerman | JP | 62-068893 | | 3/1987 |
| 2010/0069786 A1 | 3/2010 | Globerman | JP | 63-194722 A | | 8/1988 |
| 2010/0152855 A1 | 6/2010 | Kuslich et al. | JP | 02-122017 | | 5/1990 |
| 2010/0268271 A1 | 7/2010 | Beyar | JP | 02-166235 | | 6/1990 |
| 2010/0268231 A1 | 10/2010 | Kuslich et al. | JP | 02-125730 U | | 10/1990 |
| 2012/0307586 | * 12/2012 | Globerman et al. ......... 366/288 | JP | 4 329956 | | 11/1992 |
| | | | JP | 07-000410 | | 1/1995 |
| FOREIGN PATENT DOCUMENTS | | | JP | 8322848 | | 12/1996 |
| DE | 136018 C | 11/1902 | JP | 10146559 | | 6/1998 |
| DE | 226956 | 3/1909 | JP | 10-511569 | | 10/1998 |
| DE | 868497 C | 2/1953 | JP | 2004-16707 | | 1/2004 |
| DE | 1283448 | 11/1968 | JP | 2008-55367 | * | 3/2008 |
| DE | 1810799 | 6/1970 | JP | 200855367 | | 3/2008 |
| DE | 2821785 | 11/1979 | RO | 116784 | | 6/2001 |
| DE | 3003947 | 8/1980 | RU | 662082 | | 5/1979 |
| DE | 2947875 | 4/1981 | RU | 1011119 | | 4/1983 |

| RU | 1049050 | 10/1983 |
| WO | WO 90/00037 | 1/1990 |
| WO | WO 92/14423 | 9/1992 |
| WO | WO 94/12112 | 6/1994 |
| WO | WO 95/13862 | 5/1995 |
| WO | WO 96/11643 | 4/1996 |
| WO | WO 96/19940 | 7/1996 |
| WO | WO 96/32899 | 10/1996 |
| WO | WO 96/37170 | 11/1996 |
| WO | WO 97/18769 | 5/1997 |
| WO | WO 97/28835 | 8/1997 |
| WO | WO 98/28035 | 7/1998 |
| WO | WO 98/38918 | 9/1998 |
| WO | WO 99/18866 | 4/1999 |
| WO | WO 99/18894 | 4/1999 |
| WO | WO 99/29253 | 6/1999 |
| WO | WO 99/37212 | 7/1999 |
| WO | WO 99/39661 | 8/1999 |
| WO | WO 99/49819 | 10/1999 |
| WO | WO 99/52446 | 10/1999 |
| WO | WO 00/06216 | 2/2000 |
| WO | WO 00/44319 | 8/2000 |
| WO | WO 00/44321 | 8/2000 |
| WO | WO 00/44946 | 8/2000 |
| WO | WO 00/54705 | 9/2000 |
| WO | WO 00/56254 | 9/2000 |
| WO | WO 01/08571 | 2/2001 |
| WO | WO 01/13822 | 3/2001 |
| WO | WO 01/54598 | 8/2001 |
| WO | WO 01/60270 | 8/2001 |
| WO | WO 01/76514 | 10/2001 |
| WO | WO 02/00143 | 1/2002 |
| WO | WO 02/02033 | 1/2002 |
| WO | WO 02/19933 | 3/2002 |
| WO | WO 02/064062 | 8/2002 |
| WO | WO 02/064194 | 8/2002 |
| WO | WO 02/072156 | 9/2002 |
| WO | WO 02/096474 | 12/2002 |
| WO | WO 03/007854 | 1/2003 |
| WO | WO 03/015845 | 2/2003 |
| WO | WO 03/022165 | 3/2003 |
| WO | WO 03/061495 | 7/2003 |
| WO | WO 03/078041 | 9/2003 |
| WO | WO 03/101596 | 12/2003 |
| WO | WO 2004/002375 | 1/2004 |
| WO | WO 2004/019810 | 3/2004 |
| WO | WO 2004/071543 | 8/2004 |
| WO | WO 2004/075965 | 9/2004 |
| WO | WO 2004/080357 | 9/2004 |
| WO | WO 2004/110292 | 12/2004 |
| WO | WO 2004/110300 | 12/2004 |
| WO | WO 2005/000138 | 1/2005 |
| WO | WO 2005/032326 | 4/2005 |
| WO | WO 2005/048867 | 6/2005 |
| WO | WO 2005/051212 | 6/2005 |
| WO | WO 2005/110259 | 11/2005 |
| WO | WO 2006/011152 | 2/2006 |
| WO | WO 2005/032326 | 4/2006 |
| WO | WO 2006/039159 | 4/2006 |
| WO | WO 2006/090379 | 8/2006 |
| WO | WO 2007/015202 | 2/2007 |
| WO | WO 2007/036815 | 4/2007 |
| WO | WO 2007/148336 | 12/2007 |
| WO | WO 2008/004229 A2 | 1/2008 |
| WO | WO 2008/032322 | 3/2008 |
| WO | WO 2008/047371 | 4/2008 |

OTHER PUBLICATIONS

Krause, "The Viscosity of Acrylic Bone Cements," J. Biomed. Mat. Res. 16:219 (1982).
Al-Assir, et al., "Percutaneous Vertebroplasty: A Special Syringe for Cement Injection," AJNR Am. J. Neuroradiol. 21:159-61 (Jan. 2000).
Amar, Arun P. et al., "Percutaneous Transpedicular Polymethylmethacrylate Vertebroplasty for the Treatment of Spinal Compression Fractures," Neurosurgery 49(5):1105-15 (2001).
Andersen, M. et al., "Vertebroplastik, ny behandling of osteoporotiske columnafrakturer?", Ugeskr Laefer 166/6:463-66 (Feb. 2, 2004).
Avalione & Baumeister III, Marks' Standard Handbook for Mechanical Engineers, 10 ed, pp. 5-6 (1996).
Baroud et al., "Injection Biomechanics of Bone Cements Used in Vertebroplasty," Biomed. Mat. & Eng. 00:1-18 (2004).
Barr, J.D., "Percutaneous Vertebroplasty for pain Relief and Spinal Stabilization," Spine 25(8):923-28 (2000).
Belkoff, S. et al., The Biomechanics of Vertebroplasty, the Effect of Cement Volume on Mechanical Behavior, SPINE 26(14):1537-41 (2001).
Belkoff, S.M. et al., "An Ex Vivo Biomechanical Evaluation of a Hydroxyapatite Cement for Use with Kyphoplasty," Am. J. Neurorad. 22:1212-16 (2001).
Belkoff, S.M. et al., "An Ex Vivo Biomechanical Evaluation of a Inflatable Bone Tamp Used in the Treatment of Compression Fracture," SPINE 26(2):151-56 (2001).
Belkoff, S.M. et al., "An In Vitro Biomechanical Evaluation of Bone Cements Used in Percutaneous Vertebroplasty, " Bone 25(2):23S-26S (1999).
Blinc, A et al., "Methyl-methacrylate bone cement surface does not promote platelet aggregation or plasma coagulation in vitro," Thrombosis Research 114:179-84 (2004).
Bohner, M. et al., "Theoretical and Experimental Model to Describe the Injection of a Polymethacrylate Cement into a Porous Structure," Biomaterials 24(16):2721-30 (2003).
Breusch, S. et al., "Knochenzemente auf Basis von Polymethylmethacrylat," Orthopade 32:41-50 (2003) w/ abs.
Canale et al., "Campbell's operative orthopaedic-vol. 3-ninth ed", Mosby:P2097,2121,2184-85,2890-96, (1998) abstracts.
Carrodegus et al., "Injectable Acrylic Bone Cements for Vertebroplasty with Improved Properties," J. Biomed. Materials Res. 68(1):94-104 (Jan. 2004).
Codman & Shurtleff, "V-MAX™ Mixing and Delivery Device," Catalog No. 43-1056, 2001.
Cole et al., "AIM Titanium Humeral Nail System," Surgical Technique. DePuy Orthopaedics 17P (2000).
Combs, S. et al., "The Effects of Barium Sulfate on the Polymerization Temperature and Shear Strength of Surgical Simplex P," Clin. Ortho. and Related Res. pp. 287-291 (Jun. 4, 1979).
Cotton, A. et al., "Percutaneous Vertebroplasty: State of the Art," Scientific Exhibit, Radiographics 18:311-20 (1998).
Dean, J.R. et al., "The Strengthening Effect of Percutaneous Vertebroplasty," Clin Radiol. 55:471-76 (2000).
Deramond, H. et al, "Percutaneous Vertebroplasty with Polymethylmethacrylate, Technique Indications and Results," Radiologic Clinics of North America 36(3) (May 1988).
Deramond, H. et al., "Temperature Elevation Caused by Bone cement Polymerization During Vertbroplasty," Bone 25(2):17S-21S (1999).
DeWijn, J.R., Characterization of Bone Cements, The Institute of Dental Materials Science and Technology and the Dept of Ortho., Catholic University, Netherlands 46:38-51 (1975).
Edeland, "Some additional suggestions for an intervertebral disc prothesis," J. Biomed. Eng. XP008072822, 7(1):57-62 (1985.
European Search Report, from EP05763930.4; mailed Sep. 11, 2008.
European Search Report, from EP09151379.6, mailed Oct. 20, 2009.
European Search Report, from EP06780252.0, mailed Oct. 29, 2009.
Farrar, D.F. et al., "Rheological Properties of PMMA Bone Cements During Curing," Biomaterials 22:3005-13 (2001).
Fessler, Richard D. et al., "Vertebroplasty," Neurosurgical Operative Atlas 9:233-240 (2000).
Gangi, A., "CT-Guided Interventional Procedures for Pain Management in the Lumbosacral Spine," Radiographics 18:621-33 (1998).
Gangi, A., "Computed Tomography CT and Fluoroscopy-Guided Vertebroplasty: Results and Complications in 187 Patients," Seminars in Interventional Radiology 16(2):137-42 (1999).
Gangi, A., "Percutaneous Vertebroplasty Guided by a Combination of CT and Fluoroscopy," AJNR 15:83-86 (1994).
Garfin, S. R. et al., "New Technologies in Spine, Kyphoplasty and Vertebroplasty for the Treatment of Painful Osteoporotic Compression Fractures," Spine 26(14:1511-15 (2001).
Gheduzzi, S. et al., "Mechanical Characterisation of Three Percutaneous Vertebroplasty Biomaterials," J. Mater Sci Mater Med 17(5):421-26 (2006).

Giannitsios, D. et al., "High Cement Viscosity Reduces Leakage Risk in Vertebroplasty," European Cells & Mat. 10 supp. 3:54 (2005).
Grados F. et al.,"Long-Term Observations of Vertebral Osteoporotic Fractures Treated By Percutaneous Vertebroplasty," Rheumatology 39:1410-14 (2000).
Hasenwinkel, J. et al., "A Novel High-Viscosity, Two-Solution Acrylic Bone Cement: Effect of Chemical Composition on Properties," J. Biomed. Materials Research 47(1):36-45 (1999).
Hasenwinkel, J. et al., "Effect of Initiation Chemistry on the Fracture Toughness, Fatigue Strength, and Residual Monomer Content of a Novel High-Viscosity, Two-Solution Acrylic Bone Cement," J. Biomed. Materials Res. 59(3):411-21 (2001).
Heini, P. et al., "Augmentation of Mechanical Properties in Osteoporatic Vertebral Bones—a Biomechanical Investigation of Vertebroplasty Efficacy With Different Bone Cements," EUR Spine J. vol. 10, pp. 164-171, Springer-Verlag (2001).
Heini, P., "Percutaneous Transpedicular Vertebroplasty with PMMA: Operative Technique and Early Results," EUR Spine J. vol. 9, pp. 445-450, Springer-Verlag (2000).
Heini et al., "The Use of a Side-Opening Injection Cannula in Vertebroplasty," Spine 27(1):105-09 (2002).
Heraeus Palacos R, 2008, Palacos R, high Viscosity Bone Cement.
Hernandez et al., "Influence of Powder Particle Size Distribution on Complex Viscosity and Other Properties of Acrylic Bone Cement for Vertebroplasty and Kyphoplasty," J. Biomed. Mat. Res. 77B:98-103 (2006).
International Preliminary Report on Patentability, from PCT/IB06/053014, dated Apr. 10, 2008.
International Search Report, from PCT/IL06/00239, mailed Jan. 26, 2007.
International Search Report, from PCT/IL05/00812, mailed Feb. 28, 2007.
International Search Report, from PCT/IB06/052612, mailed Oct. 2, 2007.
International Search Report, from PCT/IL07/00484, mailed Apr. 17, 2008.
International Search Report, for PCT/MX03/000027, filed Mar. 14, 2003.
Ishikawa et al., "Effects of Neutral Sodium Hydrogen Phosphate on Setting Reaction and Mechanical Strength of Hydroxyapatite Putty," J. Biomed. Mat. Res. 44:322-29, 1998.
Ishikawa et al., "Non-Decay Type Fast-Setting Calcium Phosphate Cement: Hydroxyapatite Putty Containing an Increased Amount of Sodium Alginate," J. Biomed. Mat. Res. 36:393-99 (1997).
Jasper, L.E. et al., "The Effect of Monomer-to-Powder Ratio on the Material Properties of Cranioplastic," Bone 25(2):27S-29S (1999).
Jensen, Mary E. et al., "Percutaneous Polymethylmethacrylate Vertebroplasty in the Treatment of Osteoporotic Vertebral Body Compression Fractures: Technical Aspects," AJNR 18:1897-1904 (1997).
Jensen, Mary E. et al., "Percutaneous Vertebroplasty in the Treatment of Osteoporotic Compression Fractures," Spine Interventions 10(3):547-568 (2000).
Johnson & Johnson Orthopaedics, The CEMVAC Method, Raynham, MA.
Kallmes, D. et al., "Radiation Dose to the Operator During Vertebroplasty: Prospective Comparison of the Use of 1-cc Syringes Versus an Injection Device," AJNR Am. J. Neuroradiol. 24:1257-60 (2003).
Kaufmann et al, "Age of Fracture and Clinical Outcomes of Percutaneous Vertebroplasty," Am. J. Neuroradiology 22:1860-63 (2001).
Krause et al., "The Viscosity of Acrylic Bone Cements," J. Biomed. Mat. Res. 16:219-43 (1982).
Kuhn, Klaus-Dieter, Bone Cements—Uptodate Comparison of Physical and Chemical Properties of Commercial Materials, Springer-Verlag Heidelberg Germany p. 7-8, 17, 38 (2000).
Kyphom Medical Professionals, KyphXProducts (Nov. 8, 2001).
Lewis, "Properties of Acrylic Bone Cement: State of the Art Review," J. Biomed. Mat. Res. Appl. Biomaterials 38(2):155-82 (p. 158 s.Viscosity) (1997).

Lewis, G. et al., "Rheological Properties of Acrylic Bone Cement During Curing and the Role of the Size of the Powder Particles," J. Biomed. Mat. Res. Appl. Biomat. 63(2):191-99 (2002).
Lewis, "Toward Standardization of Methods of Determination of Fracture Properties of Acrylic Bone Cement and Statistical Analysis of Test Results," J. Biomed. Research: Appl. Biomaterials 53(6):748-68 (2000).
Li, C. et al., "Thermal Characterization of PMMA-Based Bone Cement Curing," J. Materials Sci.: Materials in Medicine 15:84-89 (2004).
Lieberman, I.H. et al., "Initial Outcome and Efficacy of Kyphoplasty in the Treatment of Painful Osteoporatic Vertebral Compression Fractures," Spine 26(14:1631-38 (2001).
Mathis, John et al., "Percutaneous Vertebroplasty: A Developing Standard of Care for Vertebral Compression Fractures," AJNR Am. J. Neurorad. 22:373-81 (2001).
Medsafe Palacos R 2007, Data Sheet : Palacos R Bone cement with Garamycin pp. 1-7; http://www.medsafe.govt.nz/profs/datasheet/p/palacosbonecements.htm.
Mousa, W.F. et al., "Biological and Mechanical Properties of PMMA-Based Bioactive Bone Cements," Biomaterials 21:2137-46 (2000).
Nussbaum et al., "The Chemistry of Acrylic Bone Cements and Implications for Clinical Use in Image-Guided Therapy," J. Vasc. Interv. Radiol. 15:121-26 (2004).
O'Brien, J. et al., "Vertebroplasty in patients with Severe Vertebral Compression Fractures: A Technical Report," AJNR 21:1555-58 (2000).
Odian, G., "Principles of Polymerization," pp. 20-23, 1991.
Padovani, B. et al., "Pulmonary Embolism Caused by Acrylic Cement: A Rare Complication of Percutaneous Vertebroplasty," AJNR 20:375-77 (1999).
Parallax Medical, Inc., Exflow Cement Delivery System (May 16, 2000).
Pascual, B. et al., "New Aspects of the Effect of Size and Size Distribution on the Setting Parameters and Mechanical Properties of Acrylic Bone Cements," Biomaterials 17(5):509-16 (1996).
Rimnac, CM, et al., "The effect of centrifugation on the fracture properties of acrylic bone cements," JB&JS 68A(2):281-87 (1986).
Robinson, R. et al., "Mechanical Properties of Poly(methyl methacrylate) Bone Cement," J. Biomed. Materials Res. 15(2):203-08 (2004).
Ryu, K. S. et al., "Dose-Dependent Epidural Leakage of Polymethylmethacrylate after Percutaneous Vertebroplasty in Patients with Osteoporotic Vertebral Compression Fractures," J. Neuro: Spine 96:56-61 (2002).
Saha, S. et a., "Mechanical Properties of Bone Cement: A Review," J. Biomed. Materials Res. 18(4):435-62 (1984).
Serbetci, K. et al., "Thermal and Mechanical Properties of Hydroxyapatite Impregnated Acrylic Bone Cements," Polymer Testing 23:145-55 (2004).
Shah, T., Radiopaque Polymer Formulations for Medical Devices; Medical Plastics and Biomaterials Special Section; Medical device & Diagnostic Industry pp. 102-111 (2000).
Steen, "Laser Surface Treatment," Laser Mat. Processing, Springer 2d ed. ch. 6:218-71 (2003).
Supp. EP Search Report, from EP Appl. No. 05763930.4, dated Sep. 11, 2008.
Supp. EP Search Report, from EP Appl. No. 06711221.9, dated Sep. 15, 2008.
Varela et al., "Closed Intramedullary Pinning of Metacarpal and Phalanx Fractures," Orthopaedics 13(2):213-15 (1990).
Vasconcelos, C., "Transient Arterial Hypotension Induced by Polymethyacrylated Injection During Percutaneous Vertebroplasty," Letter to the Editor, JVIR (Aug. 2001).
Weissman et al., "Trochanteric Fractures of the Femur Treatment with a Strong Nail and Early Weight-Bearing," Clin. Ortho. & Related Res. 67:143-50 (1969).

Wimhurst, J.A., et al., "The Effects of Particulate Bone Cements at the Bone-Implant Interface," J. Bone & Joint Surgery pp. 588-92 (2001).

Wimhurst, J.A. et al., "Inflammatory Responses of Human Primary Macrophages to Particulate Bone Cements in Vitro," J. Bone & Joint Surgery 83B:278-82 (2001).

Zapalowicz, K. et al., "Percutaneous Vertebroplasty with Bone Cement in the Treatment of Osteoporotic Vertebral Compression Fractures," Ortopedia Traumatologia Rehabilitacja NR Jan. 2003.

Feldman, H., "Die Geschichte der Injektionen," Laryngo-Rhino-Othol 79:239-46 (2000).

Glasgow Medico-Chirurgical Society, The lancet 1364 (May 18, 1907).

Greenberg, "Filling Root Canals by an Injection Technique," Dental Digest 61-63 (Feb. 1963).

Greenberg, "Filling Root Canals in Deciduous Teeth by an Injection Technique," Dental Digest 574-575 (Dec. 1961).

Greig, D., "A New Syringe for Injecting Paraffin," The Lancet 611-12 (Aug 29, 1903).

Lake, R., "The Restoration of the Inferior Turbinate Body by Paraffin Injections in the Treatment of Atrophic Rhinitis," The Lancet 168-69 (Jan. 17, 1903).

Paget, S., "The Uses of Paraffin in Plastic Surgery," The Lancet 1354 (May 16, 1903).

Walton, A, "Some Cases of Bone Cavities Treated by Stopping With Paraffin," The Lancet 155 (Jan 18, 1908).

International Search Report, from corresponding PCT/IL07/01257, dated Jul. 15, 2008.

Baroud, G., "Influence of Mixing Method on the Cement Temperature—Mixing Time History and Doughing Time of Three Acrylic Cements for Vertebroplasty," Wiley Periodicals Inc. 112-116 (2003).

European Search Report, from EP10182769.9, mailed Mar. 2, 2011.
European Search Report, from EP10182693.1, mailed Mar. 2, 2011.
European Search Report, from EP10192302.7, mailed Mar. 24, 2011.
European Search Report, from EP10192301.9, mailed Mar. 24, 2011.
European Search Report, from EP10192300.1, mailed Mar. 24, 2011.

Hide, I. et al., "Percutaneous Vertebroplasty: History, Technique and current Perspectives," Clin. Radiology 59:461-67 (2004).

Hu, M. et al., "Kyphoplasty for Vertebral Compression Fracture Via a Uni-Pedicular Approach," Pain Phys. 8:363-67 (2005).

International Search Report, for PCT/IL07/00808, issued Aug. 22, 2008.

Liang, B. et al, "Preliminary Clinical Application of Percutaneous Vertebroplasty," Zhong Nan Da Xue Bao Yi Xue Ban 31(1):114-9 (2006)(abs. only).

Marks, Standard handbook for mechanical engineers, section 5 (Tenth ed. 1996).

Noetzel, J. et al., Calcium Phosphate Cements in Medicine and Denistry—a Review of Literature, Schweiz Monatsschr Zehmed 115(12):1148-56 (2005)(abs. only).

Supp. EP Search Report, from EP Appl. No. 07766863.0, dated Apr. 12, 2011.

Supp. EP Search Report, from EP 07766838.2, dated May 18, 2011.

Cromer, A., "Fluids," Physics for the Life Sciences, 2:136-37 (1977).

JP Office Action, from JP Appl No. 2008-532910, mailed Jul. 19, 2011.

Lindeburg, M., "External Pressurized Liquids," Mechanical Eng. Ref. Manual for the PE Exam, 10:15-14(May 1997).

JP Office Action, from JP Appl No. 2009-517607, mailed Aug. 9, 2011.

European Search Report, from EP07827231.7, mailed Sep. 12, 2011.

Japanese Office Action issued Dec. 6, 2011 for Application No. 2008-524651 (9 pages).

Mendizabal et al., Modeling of the curing kinetics of an acrylic bone cement modified with hydroxyapatite. International Journal of Polymeric Materials. 2003;52:927-938.

Morejon et al., Kinetic effect of hydroxyapatite types on the polymerization of acrylic bone cements. International Journal of Polymeric Materials. 2003;52(7):637-654.

Sreeja et al., Studies on poly(methyl methacrylate)/polystyrene copolymers for potential bone cement applications. Metals Materials and Processes. 1996;8(4):315-322.

Yang et al., Polymerization of acrylic bone cement investigated by differential scanning calorimetry: Effects of heating rate and TCP content. Polymer Engineering and Science. Jul. 1997;1182-1187.

Japanese Office Action issued Feb. 21, 2012 for Application No. 2009-516062 (6 Pages).

Japanese Office Action for Application No. 2009-517607, dated Aug. 28, 2012. (4 pages).

European Search Report for Application No. 12181745.6, issued Sep. 25, 2012. (9 pages).

* cited by examiner

US 8,360,629 B2

MIXING APPARATUS HAVING CENTRAL AND PLANETARY MIXING ELEMENTS

RELATED APPLICATIONS

The present application claims the benefit under 119(e} of U.S. provisional patent applications U.S. 60/738,556, filed on Nov. 22, 2005, U.S. 60/762,789, filed on Jan. 26, 2006; and U.S. 60/765,484, filed on Feb. 2, 2006 all of which are entitled "METHODS, MATERIALS AND APPARATUS FOR TREATING BONE AND OTHER TISSUE".

The present application is also a continuation in part of U.S. patent application Ser. No. 11/360,251 entitled "METHODS, MATERIALS AND APPARATUS FOR TREATING BONE AND OTHER TISSUE", filed on Feb. 22, 2006, published on Feb. 1, 2007, under U.S. Publ. No 2007/0027230.

FIELD OF THE INVENTION

The present invention relates to mixing apparatus and to methods of mixing.

BACKGROUND OF THE INVENTION

Mechanical mixers for mixing components to homogeneity are well known. Their applications include, but are not limited to, baking, building construction and medicine.

Mixing apparatus for high viscosity mixtures must be adapted to provide sufficient shear force to continue moving against great resistance. In some cases, the resistance increases during mixing because the viscosity of the mixture increases.

One example of a case where the viscosity of the mixture increases during mixing is preparation of a polymer/monomer mixture. When a polymer and monomer are combined, a polymerization reaction begins. The polymerization reaction increases the average polymer chain length in the mixture and/or causes cross-linking between polymer chains. Increased polymer chain length and/or cross linking between polymer chains contribute to increased viscosity Polymerization mixtures are often employed in formulation of bone cement. One common polymer/monomer pair employed in bone cement formulation is polymethylmethacrylate/methylmethacrylate (PMMA/MMA). Because PMMA/MMA bone cements typically set to a solid form, reaction conditions for the polymerization reaction are generally adjusted so that mixing PMMA and MMA produces a liquid phase which lasts several minutes. This is typically achieved by mixing a monomer liquid including MMA and, optionally DMPT and/or HQ, with a polymer powder including PMMA and, optionally Barium Sulfate and/or BPO and/or styrene. As a result, previously available mixing equipment is constructed for use with a liquid polymerization mixture and is not well suited to mixing of highly viscous cements that have substantially no liquid phase during mixing.

The following references are cited as being generally indicative of mixer types which are currently available for use in preparation of bone cement. The list does not purport to be exhaustive.

U.S. Pat. No. 5,302,020; US 2003/0174576; U.S. Pat. No. 6,994,465 and U.S. Pat. No. 4,961,647 disclose use of a central mixing element in combination with a planetary mixing element which revolves around the central mixing element. The disclosure of each of these patents is fully incorporated herein by reference.

U.S. Pat. No. 5,415,474 and U.S. Pat. No. 7,029,163 disclose a transfer mechanism as part of a mixing apparatus. The disclosure of each of these patents is fully incorporated herein by reference.

U.S. Pat. No. 5,549,381 discloses a wiper which removes adhering mixture from a ribbon configuration mixing element as the mixing element is removed from the mixing apparatus. The disclosure of this patent is fully incorporated herein by reference.

SUMMARY OF THE INVENTION

A broad aspect of some embodiments of the present invention relates to mixing of highly viscous materials in small batches. In an exemplary embodiment of the invention, "highly viscous" indicates a viscosity of 500, 700 or 900 Pascal/second or lesser or greater or intermediate viscosities. Exemplary means of determining viscosity are set forth in Krause et al. (1982) "The viscosity of acrylic bone cements", Journal of Biomedical Materials Research, 16:219-243) which is fully incorporated herein by reference. Optionally, this viscosity is achieved within 30, 60, or 90 seconds of onset of mixing. However, under some circumstances the mixing may take a longer time. A small batch may be 100, 50, 25, 15 or 5 ml or lesser or intermediate volumes at the completion of mixing.

In an exemplary embodiment of the invention, the highly viscous material is a bone filler or "bone cement". Optionally, the bone cement includes a polymeric material, for example polymethylmethacrylate (PMMA). Optionally, the bone cement is of a type described in one or more of U.S. patent applications U.S. 60/738,556; U.S. 60/762,789; 60/765,484 and Ser. No. 11/360,251. The disclosures of these applications are fully incorporated herein by reference.

An aspect of some embodiments of the present invention relates to a mixer for a small batch of a highly viscous material including a drive mechanism employing a stationary circumferential gear on an inner surface of a mixing well. In an exemplary embodiment of the invention, the stationary circumferential gear drives a planetary mixing element. The planetary mixing element travels circumferentially around the mixing well while rotating with respect to its own axis.

In an exemplary embodiment of the invention, the planetary mixing element mixes the material in conjunction with a central mixing element. In an exemplary embodiment of the invention, the central mixing element is positioned substantially in a center of a mixing well. Optionally, the central mixing element and/or the planetary mixing element rotate on their own axes.

In an exemplary embodiment of the invention, rotation of the planetary mixing element and the central mixing element is characterized by different radial velocities with respect to their respective axes.

In an exemplary embodiment of the invention, rotation of the planetary mixing element and the central mixing element is in opposite directions on their respective axes.

An aspect of some embodiments of the present invention relates to a mixer for a small batch of viscous material including at least one planetary mixing element which revolves around a central mixing element deployed substantially at a center of the mixing well, wherein a distance (d) between outer surfaces of the mixing elements and between the planetary mixing element and an inner wall of the mixing well is substantially equivalent.

An aspect of some embodiments of the present invention relates to a mixer for a small batch of viscous material characterized by a gear ratio between a stationary circumferential gear and a gear of a planetary mixing element selected to produce a desired shearing force on a mixture.

An aspect of some embodiments of the present invention relates to a mixer for a small batch of viscous material characterized by mixing elements of a size selected to produce a desired shearing force on a mixture.

In an exemplary embodiment of the invention, for a desired shear force, the selected gear ratio increases as (d) increases. In an exemplary embodiment of the invention, for a desired shear force, the selected gear ratio increases as a diameter of a mixing well increases.

An aspect of some embodiments of the present invention relates to a method of mixing components of a small batch of a mixture with a viscosity of at least 500 Pascal/second including operating a manual drive mechanism to cause a planetary mixing element to rotate about its own axis and to revolve around a central mixing element.

An aspect of some embodiments of the present invention relates to use of a wiping element to automatically separate a viscous material from at least one mixing element of a mixing apparatus as the mixing element is removed from the apparatus so that the viscous material is retained in the apparatus. In an exemplary embodiment of the invention, the wiping element includes at least one wiping aperture which substantially conforms to a mixing element. Optionally, the wiping aperture is round, optionally substantially circular. In an exemplary embodiment of the invention, the wiping element revolves within the mixing well during operation of the drive mechanism.

An aspect of some embodiments of the present invention relates to an apparatus for transferring a viscous material from a first container to a second container. In an exemplary embodiment of the invention, the apparatus is adapted for use with bone cement. Optionally, the first container is a mixing well and the second container is a portion of an injection apparatus. In an exemplary embodiment of the invention, manual manipulation of components of the apparatus produces sufficient force to cause a material characterized by a viscosity of 500 Pascal/sec to flow through an aperture between the first container and the second container.

According to various embodiments of the invention, a desired shear force for a small batch of viscous material may be produced by varying one or more of:

a) roughness of surfaces in a mixing well and/or on mixing elements, to create a boundary layer;

b) distances between the surfaces, wherein smaller distances contribute to increased shear force;

c) relative velocities of surfaces of mixing elements and/or surface of the mixing well.

Relative velocities are optionally influenced by one or more of, dimensions, gear ratio, drive speed and rotation velocity of mixing elements.

In an exemplary embodiment of the invention, there is provided a mixing apparatus, the apparatus includes:

a) a mixing well characterized by an internal volume not exceeding 100 ml.;

b) a drive mechanism including a stationary circumferential gear on an inner surface of the mixing well; and c) a planetary mixing element driven by a mixing element gear which engages the stationary circumferential gear.

Optionally, the drive mechanism is adapted to provide sufficient shear force to mix a mixture characterized by a viscosity of at least 500 Pascal/second.

Optionally, the viscosity of at least 500 Pascal/second is achieved within 90 seconds of an onset of mixing.

Optionally, the apparatus includes:

d) a cover engageable by the mixing well and adapted for closure thereof.

Optionally, the cover includes a locking ring.

Optionally, the drive mechanism is adapted for manual operation.

Optionally, the apparatus includes:

d) a wiping element adapted to concurrently engage an inner surface of the mixing well and the planetary mixing element.

Optionally, the apparatus includes:

d) a central mixing element positioned substantially at a center of the mixing well.

Optionally, the apparatus includes:

e) a wiping element adapted to concurrently engage an inner surface of the mixing well, the planetary mixing element and the central mixing element.

Optionally, the central mixing element rotates about its own axis.

Optionally, the central mixing element and the planetary mixing element rotate in opposite directions.

In an exemplary embodiment of the invention, there is provided a mixing apparatus, the apparatus includes:

a) a mixing well characterized by an internal volume not exceeding 100 ml.;

b) a drive mechanism adapted to operate at least one mixing element positioned in the mixing well; and c) a wiping element adapted to engage an inner surface of the mixing well and including at least one wiping aperture substantially conforming to the at least one mixing element;

wherein the wiping element does not interfere with operation of the drive mechanism; and wherein the withdrawal of the at least one mixing element from the mixing well causes the at least one wiping aperture to remove at least a portion of the mixture from the at least one mixing element.

Optionally, the wiping element rotates within the mixing well while engaging an inner surface thereof.

Optionally, the drive mechanism is adapted to provide sufficient shear force to mix a mixture characterized by a viscosity of at least 500 Pascal/second.

Optionally, the apparatus includes:

d) a cover engageable by the mixing well and adapted for closure thereof.

Optionally, the cover includes a locking ring.

Optionally, the viscosity of at least 500 Pascal/second is achieved within 90 seconds of an onset of mixing.

Optionally, the wiping element is adapted to remove an adherent portion of a mixture characterized by a viscosity of at least 500 Pascal/second from the at least one mixing element.

Optionally, the at least one mixing element includes at least two mixing elements.

Optionally, the drive mechanism is adapted for manual operation.

In an exemplary embodiment of the invention, there is provided a mixing apparatus, the apparatus includes:

a) a mixing well characterized by an internal volume not exceeding 100 ml.;

b) a central mixing element deployed substantially at a center of the mixing well;

c) at least one planetary mixing element which revolves around the central mixing element;

wherein a first distance ($d_1$) between the central mixing element and the planetary mixing element is substantially equivalent to a second distance ($d_2$) between the planetary mixing element and an inner surface of the mixing well.

Optionally, the drive mechanism is adapted for manual operation.

Optionally, the drive mechanism is adapted to provide sufficient shear force to mix a mixture characterized by a viscosity of at least 500 Pascal/second.

In an exemplary embodiment of the invention, there is provided a drive mechanism for a mixing apparatus, the drive mechanism includes;

a) a set of teeth defining a circular path on an inner circumference of a vessel characterized by an internal volume not exceeding 100 ml;

b) a toothed wheel characterized by an axis, the wheel adapted to engage said set of teeth and to rotate about the axis; and c) an actuator adapted to provide a force which causes the toothed wheel to advance along the circular path.

Optionally, the mechanism includes d) a drive transfer element connecting between the axis of the toothed wheel and a second wheel positioned substantially at a center of the circular path.

Optionally, provision of a force through the actuator causes the drive transfer element to rotate the second wheel about an axis through the center of the circular path.

Optionally, the toothed wheel drives a planetary mixing element.

Optionally, the second wheel drives a central mixing element.

Optionally, the actuator is manually powered.

Optionally, the mechanism is adapted to provide sufficient shear force to mix a mixture characterized by a viscosity of at least 500 Pascal/second.

In an exemplary embodiment of the invention, there is provided a method of mixing components of a viscous mixture, the method includes:

a) placing the components in a mixing well characterized by an inner volume of not more than 100 ml;

b) deploying at least one planetary mixing element and a central mixing element in the mixing well; and c) operating a manual drive mechanism to cause the planetary mixing element to both rotate about its own axis and revolve around the central mixing element in order to mix the components to form a mixture.

Optionally, the method includes:

e) engaging a wiping element to at least one of the mixing elements such that withdrawal of the mixing element from the mixing well causes the wiping element to wipe mixture from the mixing element.

Optionally, the drive mechanism is adapted to provide sufficient shear force to mix a mixture characterized by a viscosity of at least 500 Pascal/second.

Optionally, the viscosity of at least 500 Pascal/second is achieved within 90 seconds of an onset of mixing.

Optionally, the manual drive mechanism supplies a sufficient force to cause the planetary mixing element to move through a mixture characterized by a viscosity of at least 500 Pascal-second.

In an exemplary embodiment of the invention, there is provided an apparatus for transferring a viscous material, the apparatus includes:

a) a first container capable of containing a viscous material;

b) a transfer piston insertable in the first container so that the piston forms a circumferential seal with respect to the container, the transfer piston including a hole; and c) a mechanism for attaching an aperture of a second container to the hole in the transfer piston;

wherein insertion of the transfer piston into the first container causes the viscous material to pass through the aperture into the second container.

Optionally, the apparatus is adapted to provide sufficient force to cause a viscous material characterized by a viscosity of at least 500 Pascal/second to flow through the aperture of the second container.

Optionally, the apparatus is configured so that manual manipulation of the first container and the transfer piston produces the sufficient force.

Optionally, the transfer piston is adapted to remove at least a portion of the viscous material from a mixing element as the mixing element is removed from the first container.

In an exemplary embodiment of the invention, there is provided a method of mixing components of a viscous mixture, the method includes:

a) placing the components in a mixing well characterized by an inner volume of not more than 100 ml;

b) operating a drive mechanism to cause mixing of the material in the inner volume during a period when the viscosity is at least 500 Pascal/sec.

Optionally, the method includes driving a planetary mixing element by means of the drive mechanism.

BRIEF DESCRIPTION OF THE DRAWINGS

Exemplary non-limiting embodiments of the invention described in the following description, read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DESCRIPTION OF EXEMPLARY EMBODIMENTS

Overview

U.S. application 60/738,556; U.S. 60/762,789; U.S. 60/765,484; and Ser. No. 11/360,251 (hereinafter "the inventor's previous applications"), the disclosures of which are each fully incorporated herein by reference, disclose polymeric bone cement formulations which are characterized by a rapid transition to a high viscosity state. According to exemplary cement formulations disclosed in these applications, mixture of monomer and polymer components produces a mixture characterized by a viscosity in the range of 400 to 500 Pascal/second substantially as soon as the polymer is wetted by the monomer. In practice, this can take as little as 30 seconds.

Previously available bone cement formulations were characterized by a relatively long liquid phase and a short working window during which the cement was suitable for injection. A new class of cement formulations, disclosed in the inventor's previous applications is characterized by a rapid transition to a high viscosity without a persistent liquid phase followed by a relatively long working window before the cement sets to solidity. The almost immediate transition to high viscosity of the new class of cement formulations disclosed in the inventor's previous applications means that high shear forces are desirable in order to assure complete mixing. For this new class of cement formulations, it is not feasible to mix components when the mixture is still in the liquid state because there is essentially no liquid state.

Because bone cement is typically prepared in small batches (e.g. 5, 10, 20, 30, 40, 50 ml or lesser or greater or intermediate volumes), these new cement formulations of the inventor's previous applications impose new constraints on bone cement mixing apparatus.

Exemplary mixing apparatus according to the present invention may also be employed with conventional bone cement formulations. Optionally, exemplary mixing apparatus according to the present invention may be employed after the polymerization reaction has progressed past the liquid phase and achieved a viscosity of 400, optionally 500 Pascal/second or lesser or greater or intermediate viscosity. Optionally, exemplary mixing apparatus according to the present invention may be employed to mix a liquid mixture by adjusting a distance between the mixing elements. Optionally, exemplary mixing apparatus according to the present invention may be employed to mix a cement prepared according to a previously known formulation after the mixture reaches viscosity of at least 100 Pascal/second.

Figure 1:
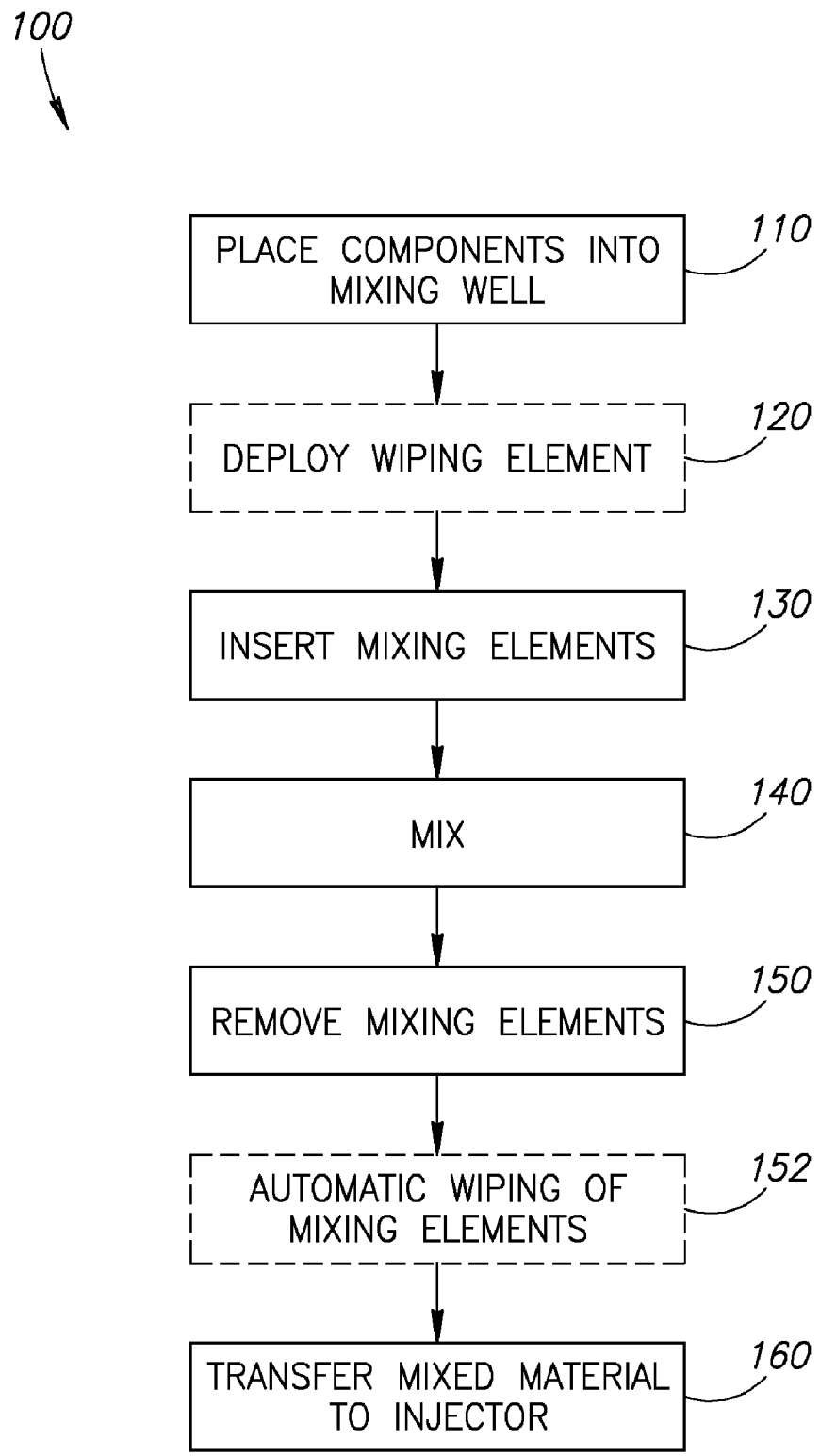
FIG. 1 is a simplified flow diagram illustrating an exemplary sequence of events associated with use of a mixing apparatus according to exemplary embodiments of the invention.

FIG. 1 is a simplified flow diagram illustrating sequence of acts associated with performance of a method 100 according to exemplary embodiments of the invention.

At 110 components are placed into a mixing well or mixing well of a mixing apparatus. Optionally this operation may be performed as part of a manufacturing procedure of apparatus 200.

Optionally, one or more wiping elements are deployed 120. Deployment may be in the mixing well or on a cover and/or on mixing elements of the mixing apparatus and may occur before or after components are placed 110 in the mixing well.

At 130 mixing elements are inserted into the mixing well so that they are at least partially submerged in components of the mixture. If a wiping element has been deployed 120, the components of the mixture are generally below the wiping element at this stage.

A drive mechanism is operated to mix 140 the components. As described hereinabove, according to exemplary embodiments of the invention, mixing 140 will cause the components to form a high viscosity mixture in a relatively short period of time, optionally in a few seconds. In an exemplary embodiment of the invention, satisfactory preparation of bone cement is achieved by continuing mixing 140 after the high viscosity mixture has been formed. Optionally, operation of the drive mechanism is manual and/or driven by a motor or by compressed air or by any other external source of force known in the art.

After mixing 140 is complete, mixing elements 150 are removed. If a wiping element has been deployed 120, automatic wiping 152 of the mixing elements occurs at this stage. Optionally, the wiping element remains in the mixing well during and/or after withdrawal 150.

Optionally, cement is transferred 160 from the mixing well to an injection reservoir directly. Optionally, transfer 160 is accomplished using transfer apparatus which comprises an exemplary embodiment of the invention.

Exemplary Apparatus

Figure 2:
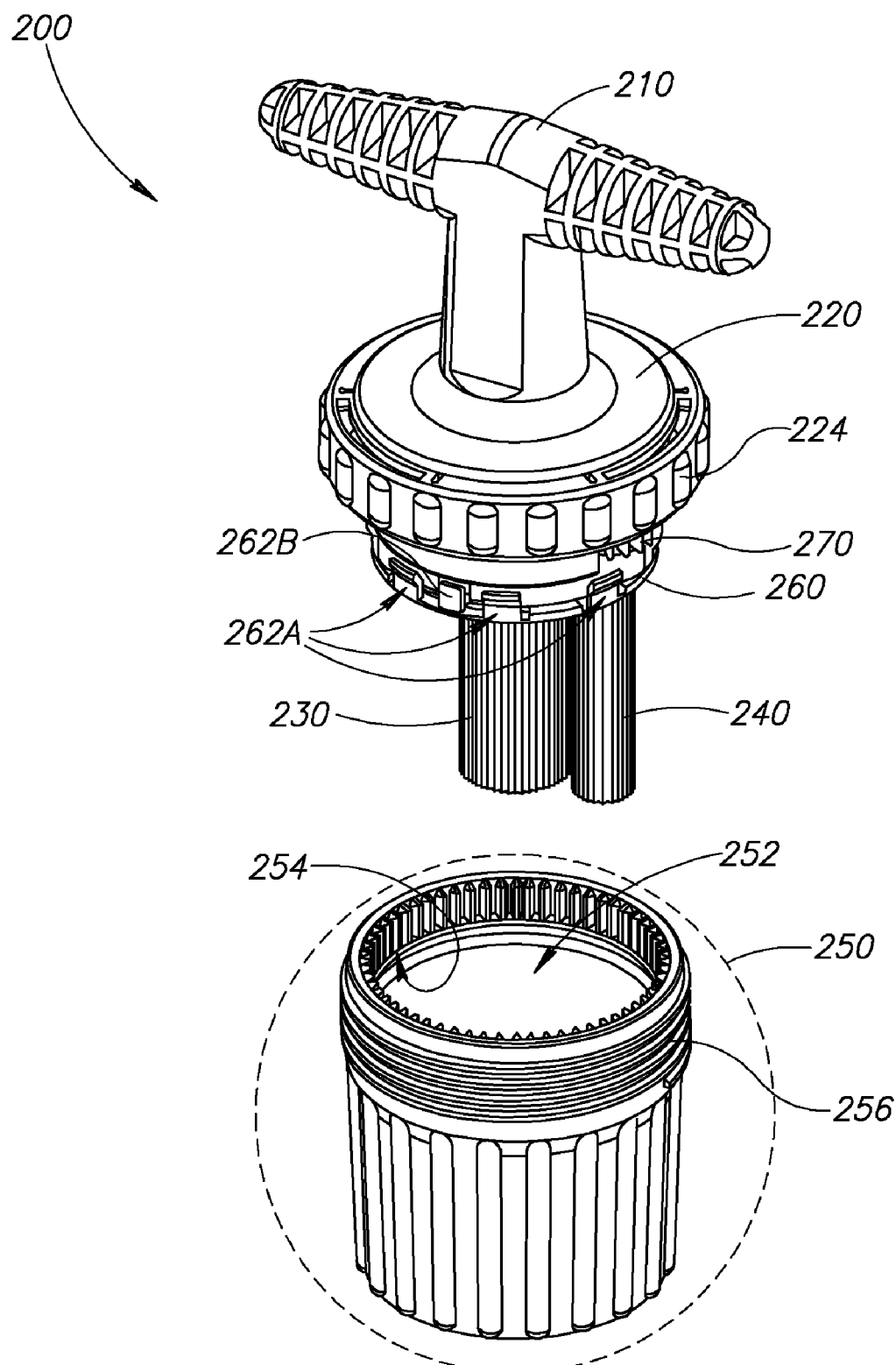
FIG. 2 is a perspective view of an exemplary mixing apparatus with the mixing elements removed from the mixing well.

FIGS. 2, 3, 6, 7 and 8 depict an exemplary embodiment of a mixing apparatus 200 according to the present invention FIG. 2 shows an exemplary apparatus 200 with a cover 220 removed from a base 250. Cover 220 is depicted with an optional locking ring 224 which mates to a set of threads 256 on base 250.

In some exemplary embodiments of the invention, components are placed 110 in a mixing well 252 at this stage.

Figure 3:
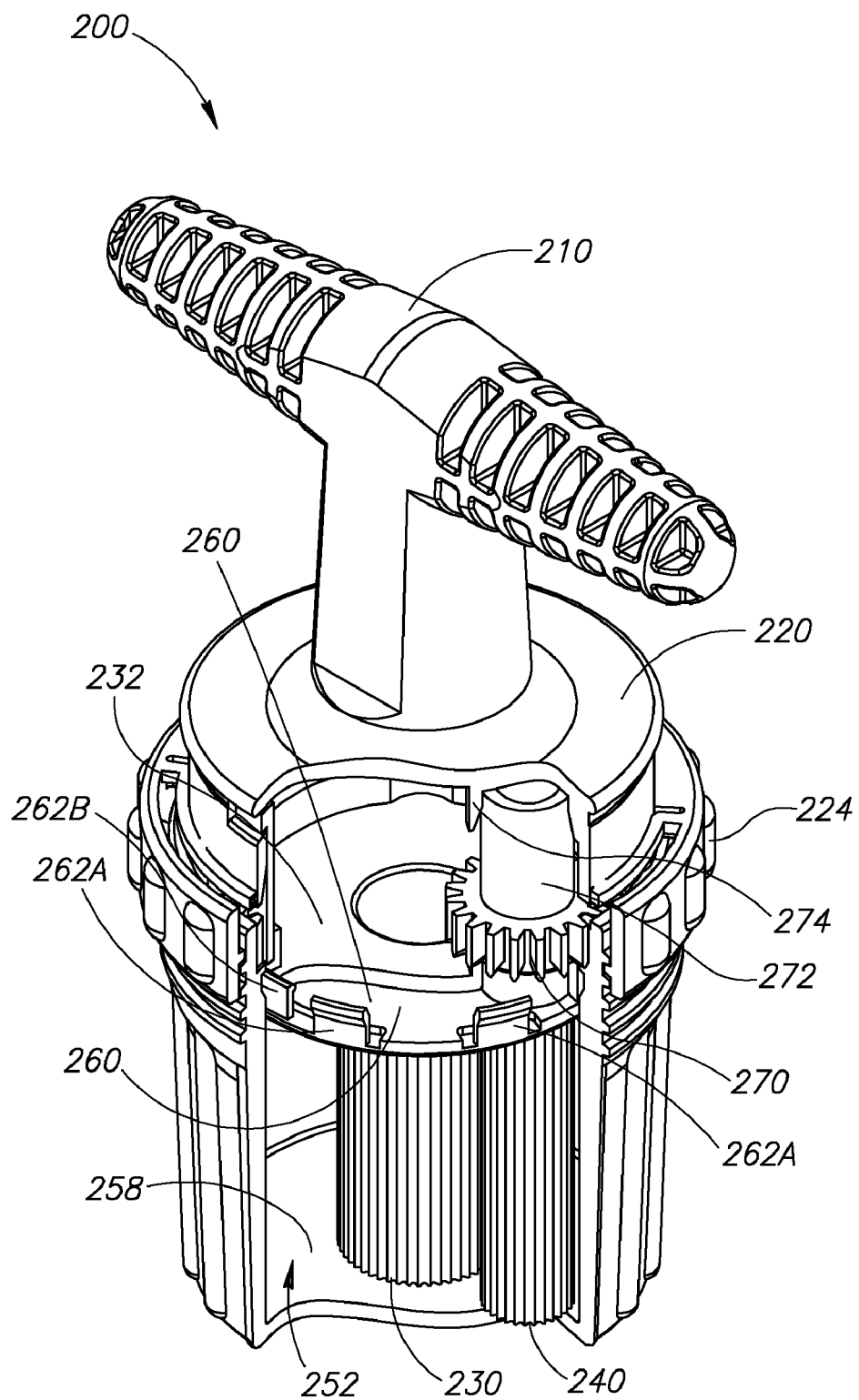
FIG. 3 partial cut away view of assembled mixer showing portion of an exemplary drive mechanism.

In other embodiments of the invention, components are placed 110 in mixing well 252 as part of a manufacturing and assembly process. Optionally, apparatus 200 is supplied assembled as depicted in FIG. 3. When apparatus 200 is supplied assembled with mixture components inside, undesired premature mixing of monomer liquid and polymer powder may be prevented by a variety of methods. Exemplary methods of preventing undesired premature mixing are described below.

Cover 220 includes portions of a drive mechanism. The drive mechanism is optionally a manual mechanism operable by a handle 210. In the pictured embodiment, cover 220 includes a downward facing protrusion 222 (FIG. 6) configured to engage a wiping element 260 by means of engagement arms 262.

In the pictured exemplary embodiment, engagement arms 262 B function primarily to engage protrusion 222.

In another exemplary embodiment, engagement arms 262 A function to engage protrusion 222 and to engage a groove 264 in base 250. A relationship between engagement arms 262 A and groove 264 in base 250 is described below.

A central mixing element 230 and a planetary mixing element 240 are visible protruding downwards from cover 220. Optionally, two or more planetary mixing elements 240 are provided. A portion of a planetary drive gear 270 is also visible in this view.

Base 250 includes an inner mixing well 252 and a series of inward facing teeth which function as a stationary circumferential gear 254. Stationary circumferential gear 254 is a part of the drive mechanism and is configured to engage planetary drive gear 270 when cover 220 is assembled with base 250.

FIG. 3 is a partial cut-away view of assembled apparatus 200 illustrating the drive mechanism in greater detail. Mixing elements 230 and 240 are inserted 130 in this view and optional wiping element 120 has been deployed in the pictured embodiment. Planetary drive gear 270 is positioned above a center axis of planetary mixing element 240 and connected thereto so that mixing element 240 travels and/or rotates together with gear 270. Gear 270 is coupled to cover 220 by drive shaft 272 seated in drive shaft receptacle 274 of cover 220. Teeth of planetary gear 270 engage complementary teeth of stationary circumferential gear 254 in mixing well 252 of base 250. Planetary mixing element 240 is coupled to central mixing element 230 by drive element 232. Wiping element 260 concurrently engages an inner surface of mixing well 252 and mixing elements 230 and 240.

Operation of the drive mechanism, for example by rotation of handle 210, causes cover 220 to rotate with respect to base 250. This causes planetary drive shaft 272 to advance on a circular path concentric to an inner wall of mixing well 252. Planetary gear 270 engages stationary circumferential gear 254 so that planetary gear 270 rotates planetary mixing element 240 as planetary drive shaft 272 and planetary mixing element 240 advance along their circular path. In an exemplary embodiment of the invention, drive element 232 is coupled to both planetary mixing element 240 and central mixing element 230. Optionally, drive element 232 causes central mixing element 230 to rotate as planetary mixing element 240 advances. In other embodiments of the invention, central mixing element 230 does not rotate. As mixing element 240 advances, mixing 140 occurs.

Figure 4B:
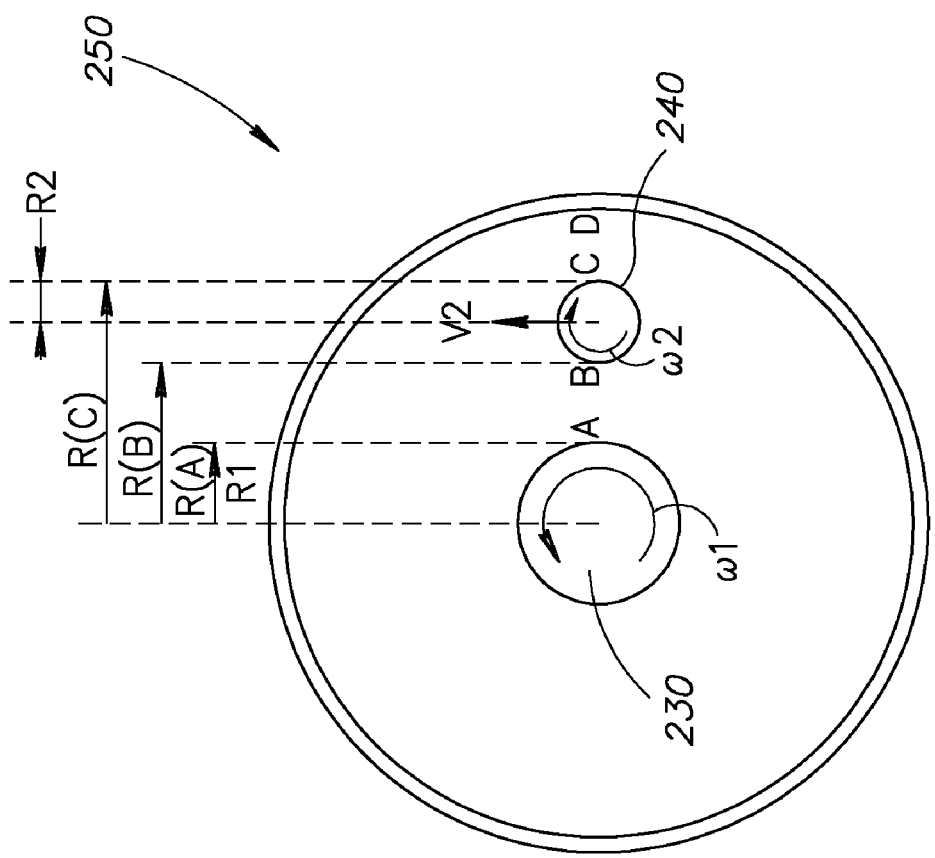
FIGS. 4A and 4B are a schematic representation and an engineering projection showing rotation direction and distances for an exemplary drive mechanism respectively.
Figure 4A:
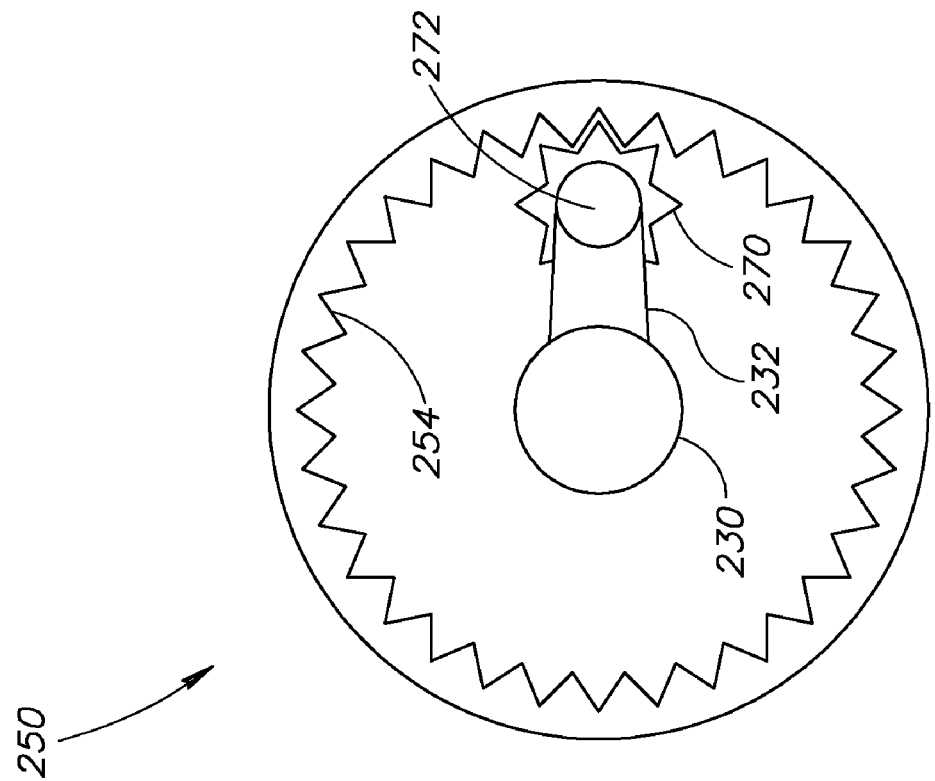

FIG. 4A is a schematic representation of an exemplary drive mechanism viewed from above base 250. The physical relationship between planetary gear 270, planetary drive shaft 272, central mixing element 230, stationary circumferential gear 254 and drive element 232 (pictured here as a lever) is more clearly visible in this view than in the preceding figure. Engineering considerations of the drive mechanism are discussed below. In an exemplary embodiment of the invention, stationary circumferential gear 254 has 3 times as many teeth as planetary drive gear 270.

Mixing elements 230 and 240 are optionally roughened, serrated or striated to insure formation of a boundary layer in the material being mixed in proximity to a surface of the mixing elements during mixing. Optionally, an inner surface of well 252 is similarly roughened, serrated or striated to insure formation of a boundary layer in proximity to a surface of the well.

In an exemplary embodiment of the invention, serrations in the form of vertical slits that extend along the full height of mixing elements 230 and/or 240. Optionally, the longitudinal slits contribute to easy introduction and removal of mixing elements 230 and/or 240 through wiping apertures in wiping element 260. Optionally, vertical slits are characterized by a depth of 0.1, 0.5 or 1 mm or lesser or greater or intermediate depths.

Exemplary Drive Mechanism Engineering considerations

FIG. 4B is an engineering projection showing rotation directions and distances for an exemplary drive mechanism respectively; The view is looking down on base 250 as for FIG. 4A.

During operation point "A" on an outer surface of central mixing element 230 will move counterclockwise (arrow) with a radial velocity V (A):

$$V(A)=\omega 1 * R1$$

where ω1 is a rotational speed of mixing element 230 in radians/sec and R1 is the radius of mixing element 230.
During operation point "B" on a surface of planetary mixing element 240 will have a radial velocity V(B) comprising the sum of velocity due to planetary mixing element 240 rotation relative to the axis of central mixing element 230 and velocity due to planetary mixing element 240 rotation on its own axis:

$$V(B)=\omega 1 * R(B)+\omega 2 * R2$$

where ω2=i*ω1
where "i" is the ratio between the number of teeth of the stationary circumferential gear 254 and the number of teeth on planetary gear 270;
and ω1 is a rotational speed of mixing element 230;
R(B) is a distance from a center of mixing element 230 to a closest point (B) on mixing element 240; and
R2 is the radius of mixing element 240
During operation point "C" on an opposite surface of planetary mixing element 240 will have a radial velocity V(C) comprising the difference between velocity due to planetary mixing element 240 rotation relative to the axis of central mixing element 230 and velocity due to planetary mixing element 240 rotation on its own axis:

$$V(C)=\omega 1 * R(C)-i * \omega 1 * R2$$

where R(C) is a distance from a center of mixing element 230 to a farthest point (C) on mixing element 240; and the remaining terms are as defined above.
Point D on stationary circumferential gear 254 will have a velocity of zero.

The shear stresses on a mixture flowing between pints A and B, or between points C and D, can be calculated by the subtraction of radial velocities between opposing points (velocity gradients):
The shear stresses between the fixed position and planetary mixing elements correlate to:

$$V(B)-V(A)=\omega 1 *(R(B)-R1+iR2)$$

The shear stresses between the planetary mixing element and to stationary mixing chamber inner surface correlate to V(C)−V(D)=ω1*(R(C)−iR2).

In an exemplary embodiment of the invention, apparatus 200 is operated manually, so ω1 is set by the operator. Optionally, ω1 can be 10, 15, 22, or 30 RPM or lesser or greater or intermediate values.

In an exemplary embodiment of the invention, R1, R2, R(B), R(C) and i, are selected to meet both geometry considerations and relatively similar velocity gradients that are sufficient to produce adequate shear stresses in consideration of a selected viscosity, such as, for example, 500 Pascal/second.

Figure 5:
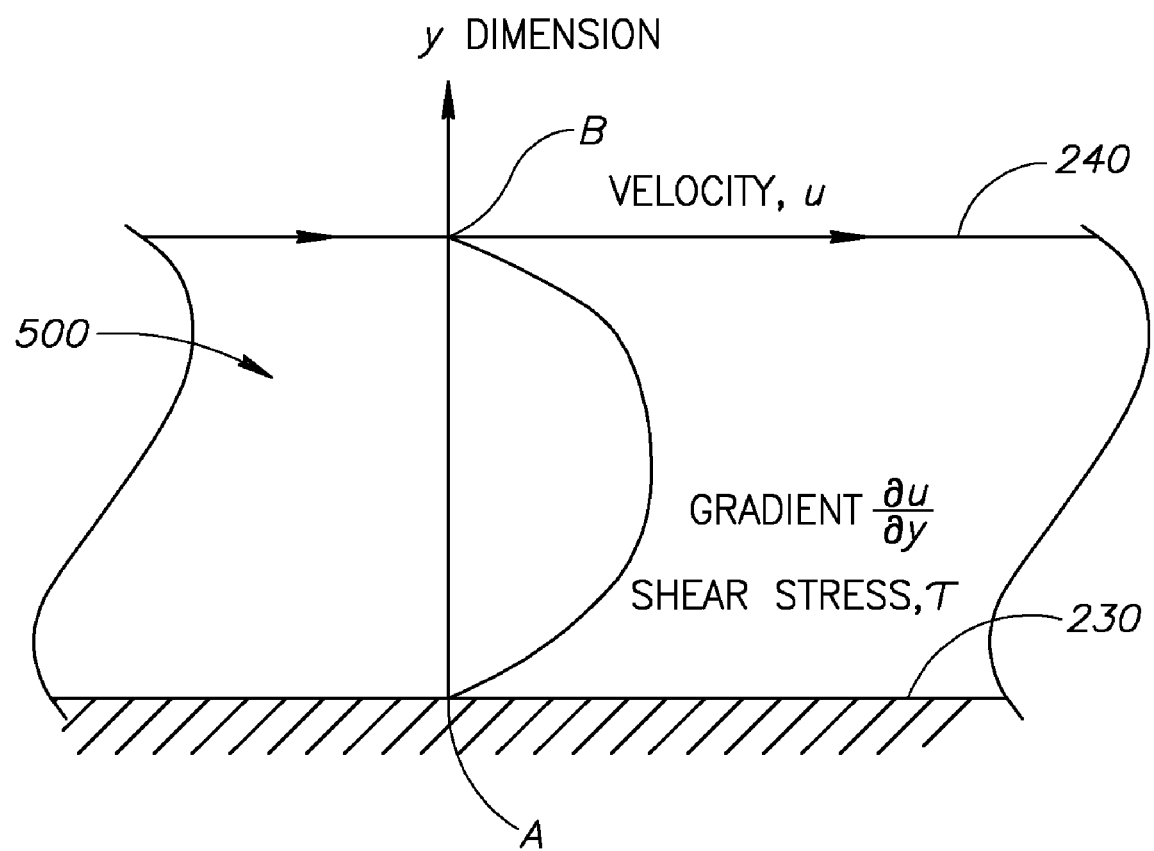
FIG. 5 is a diagram illustrating shear stress gradients between a planetary mixing element and a central mixing element according to exemplary embodiments of the invention.

FIG. 5 illustrates a theoretic gradient of the shear stress applied to a mixture 500 flowing between a two elements (e.g. planetary mixing element 240 and central mixing element 230 or planetary mixing element 240 and an inner wall of mixing well 254). As the viscosity of mixture 500 increases, the shear stress necessary for mixing also increases.

In an exemplary embodiment of the invention, sufficient shear force to mix a mixture 500 characterized by a viscosity of 500 Pascal/second is provided by adjusting distance between the two mixing elements (A to B in FIG. 4B) or between planetary mixing element 240 and an inner wall of mixing well 254 (C to D in FIG. 4B) to 1 to 5 mm, optionally about 2 mm. Alternatively or additionally, shear force may be adjusted by varying the surface area of mixing elements 230 and/or 240 and/or an inner surface of well 252 which contacts the mixture.

Wiping Element

Figure 6:
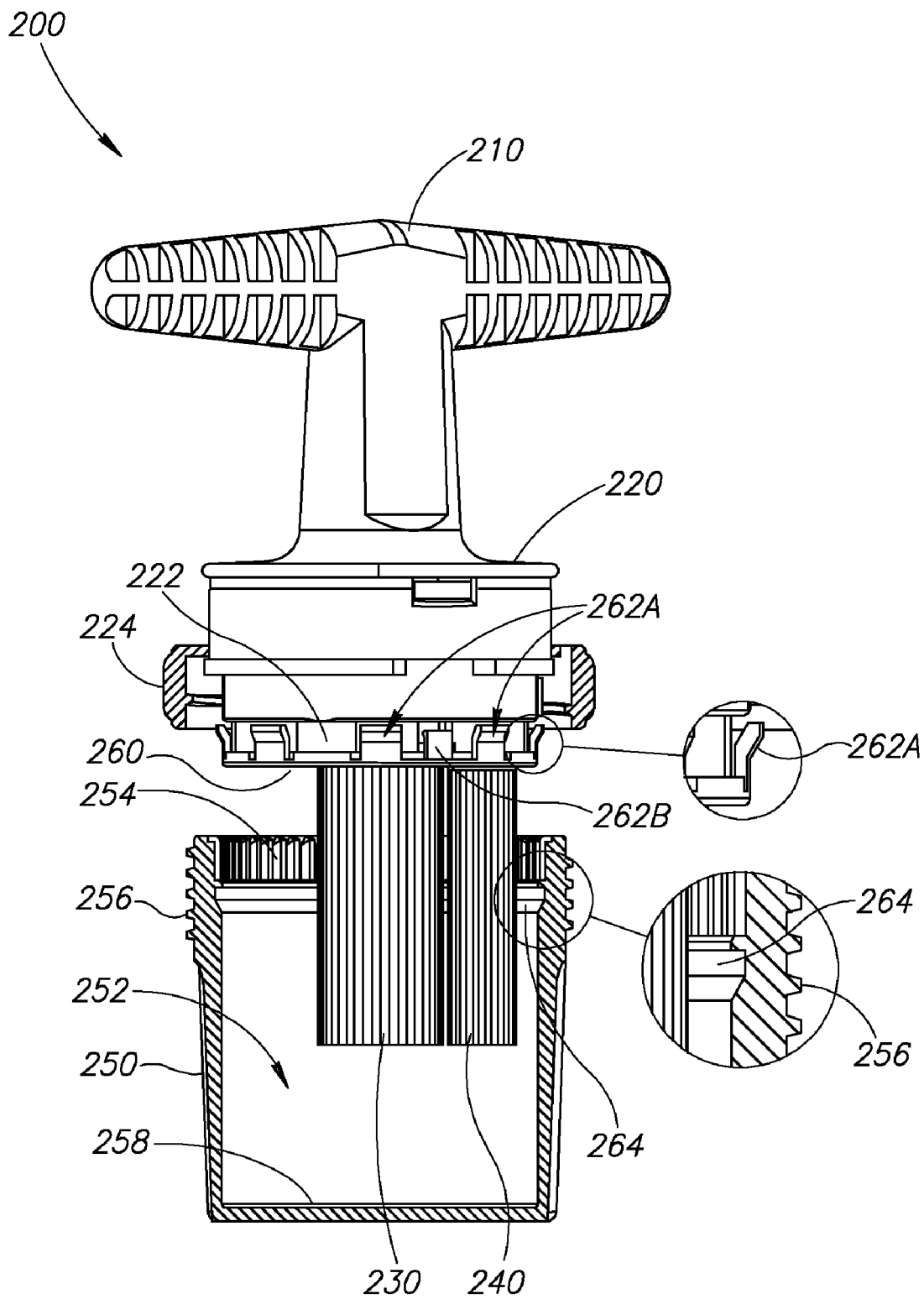
FIGS. 6, 7 and 8 illustrate an exemplary wiping element adapted for use with an exemplary mixing apparatus.
Figure 7:
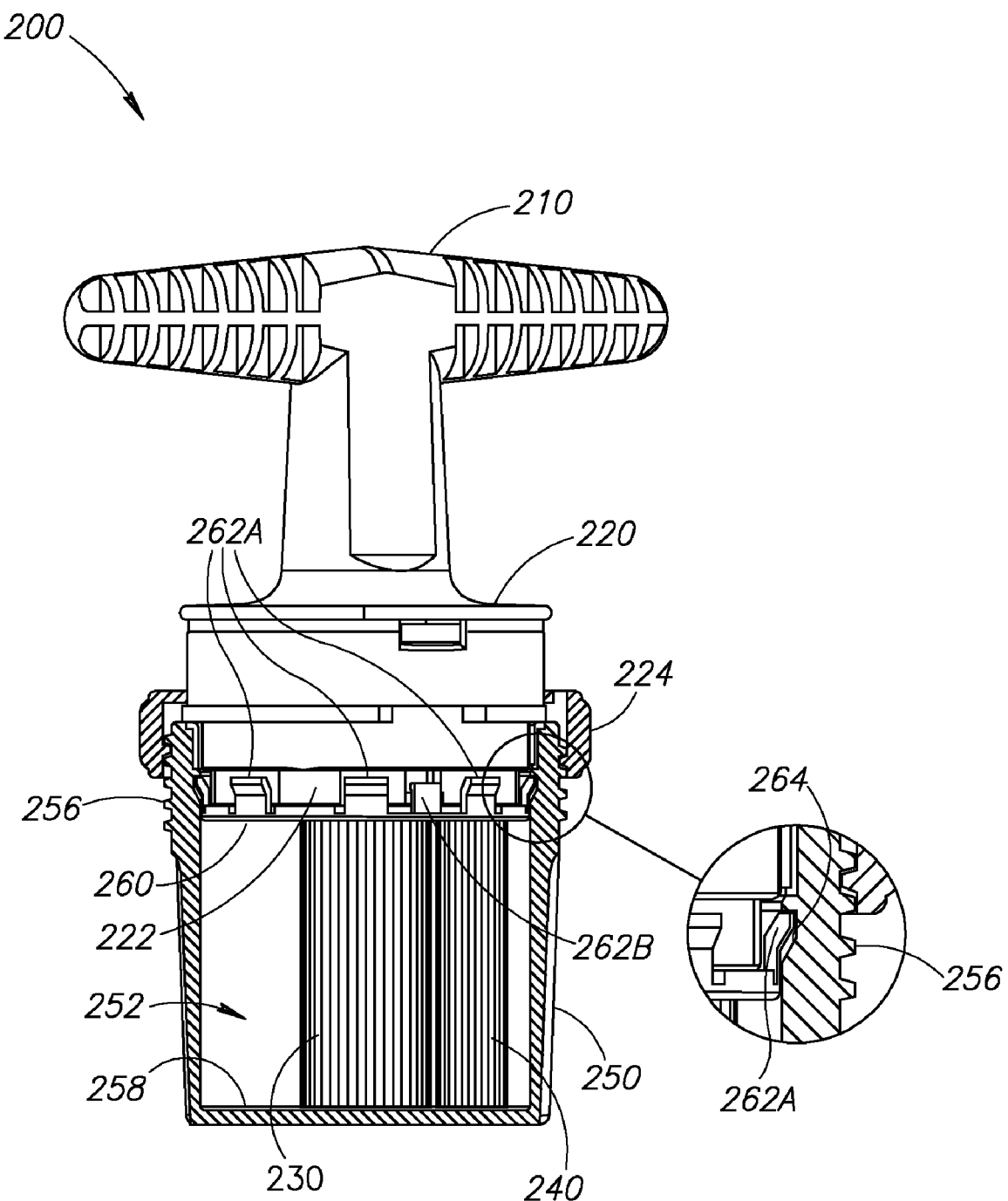
Figure 8:
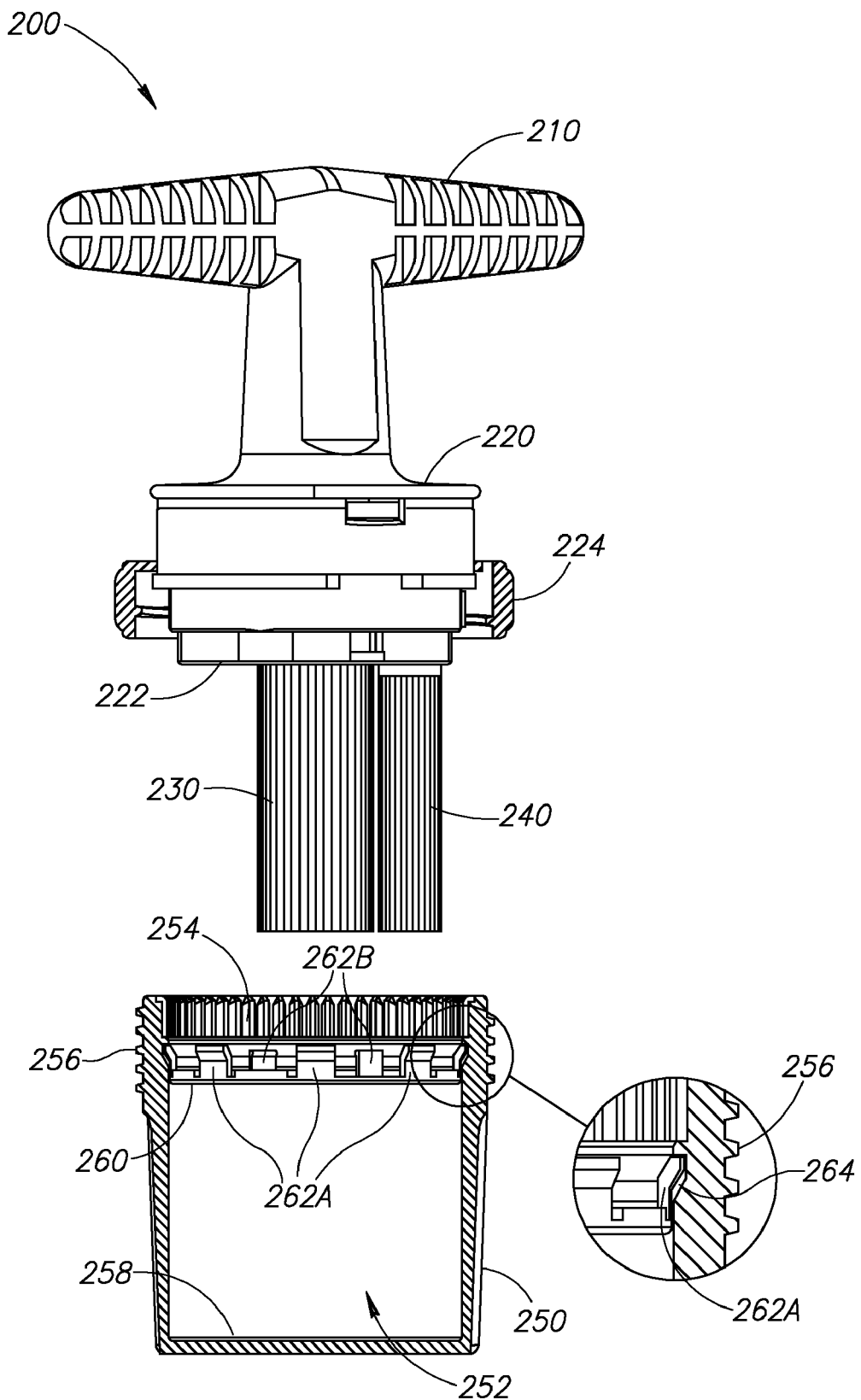

FIGS. 6, 7 and 8 illustrate placement and function of optional wiping element 260 according to an exemplary embodiment of the invention.

FIG. 6 illustrates wiping element 260 engaging downward facing protrusion 222 by means of engagement arms 262 A and 262 B. Circumferential groove 264 of mixing well 252 is empty at this stage. Mixing elements 230 and 240 protrude through wiping apertures in wiping element 260.

FIG. 7 illustrates cover 220 assembled on base 250 so that wiping elements 230 and 240 are in close proximity to floor 258 of mixing well 252. Engagement arms 262 of wiping element 260 are seated in groove 264 of mixing well 252 (magnified in inset for clarity). Each of engagement arms 262 slides circumferentially around mixing well 252 in groove 264 as planetary mixing element 240 travels around mixing well 252.

FIG. 8 illustrates removal 150 of mixing elements 230 and 240 from mixing well 252. Engagement arms 262 are retained by groove 264 so that wiping element is locked into position.

Removal of elements 230 and 240 results in automatic wiping 152 by the edges of the wiping apertures.

Transfer Mechanism

Figure 9:
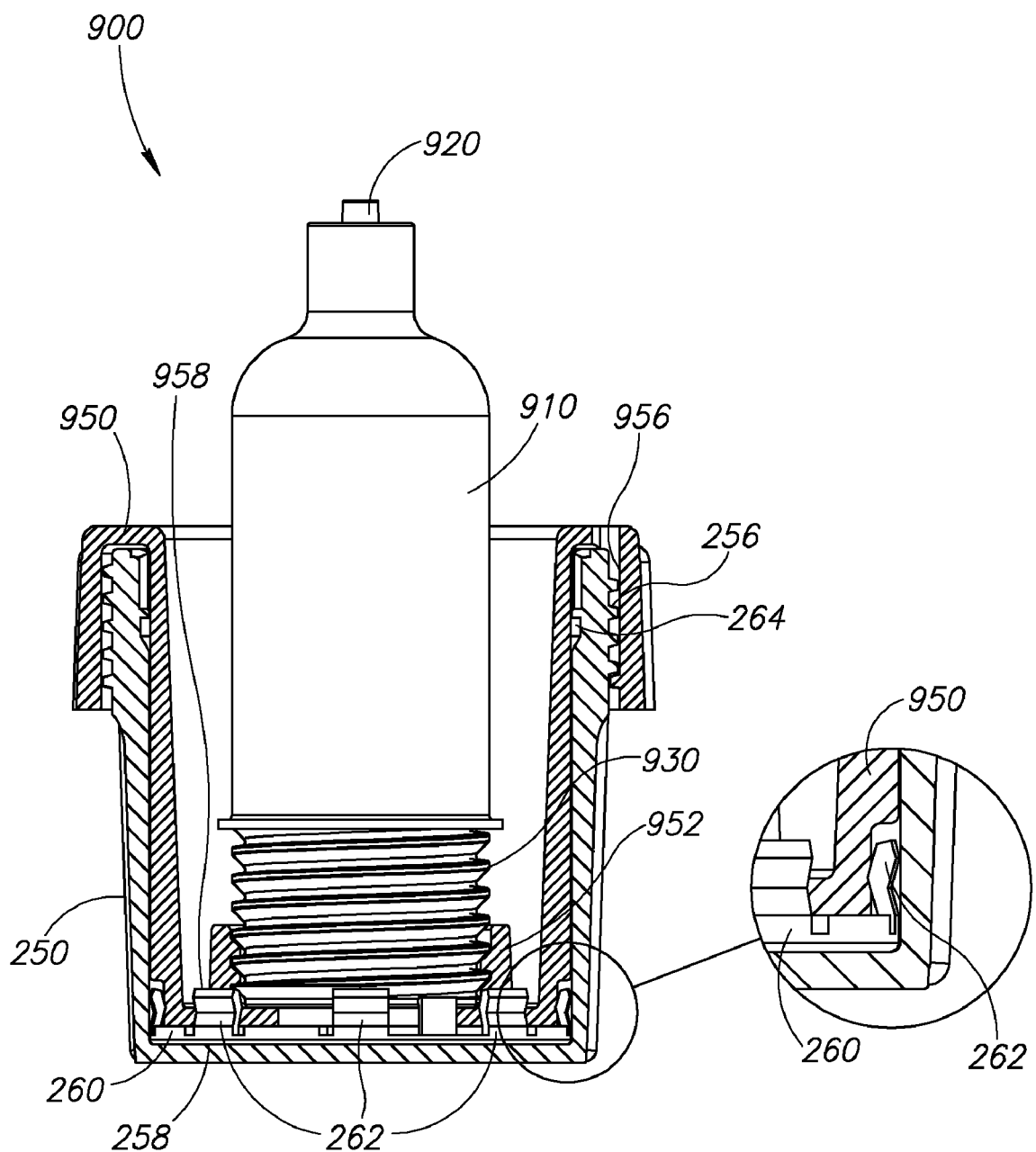
FIGS. 9 and 10 illustrate a transfer module adapted for use with exemplary mixing apparatus.
Figure 10:
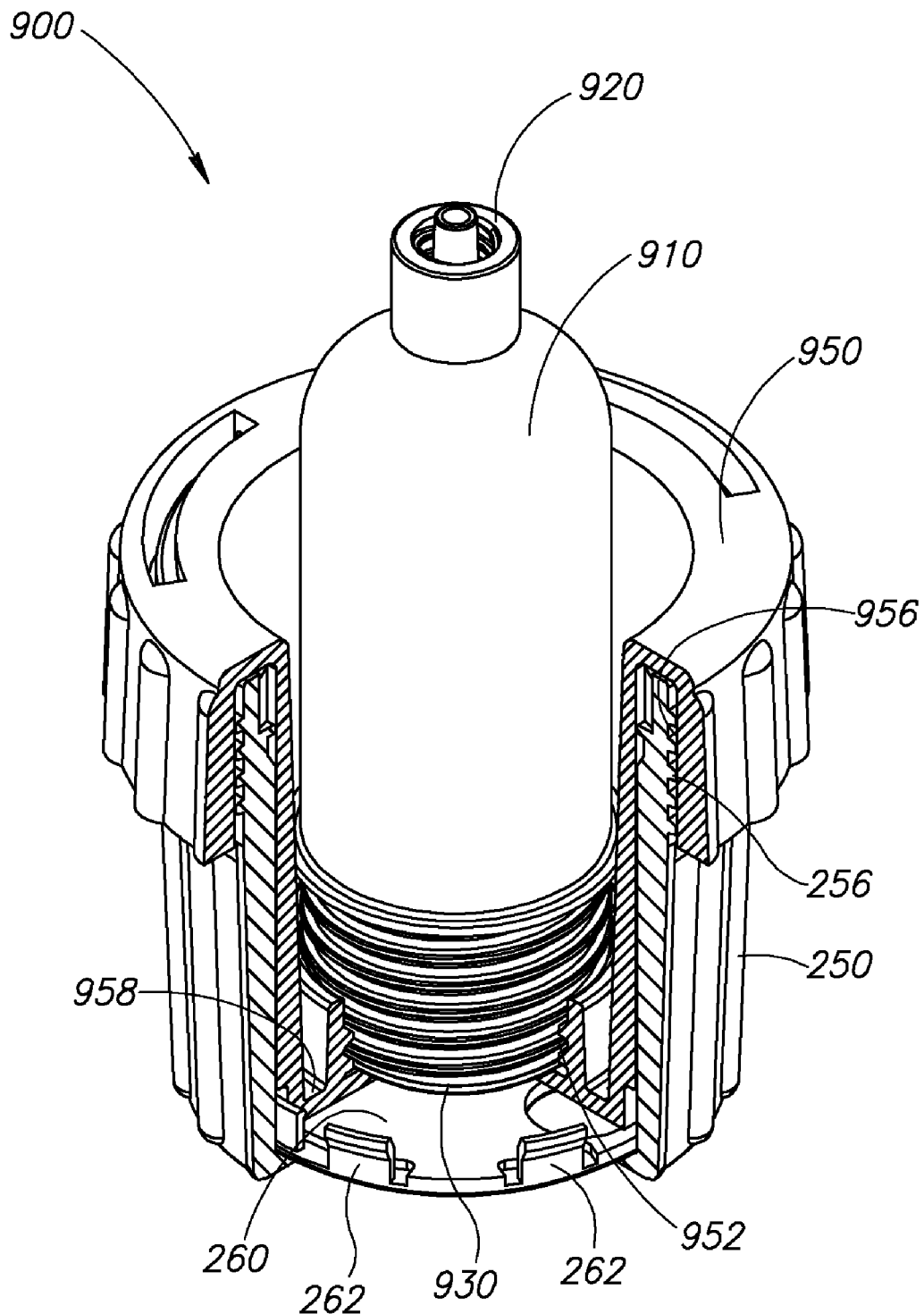

FIGS. 9 and 10 illustrate a transfer mechanism according to exemplary embodiments of the invention as previously disclosed in co-pending U.S. application Ser. No. 11/360,251, the disclosure of which is fully incorporated herein by reference. FIG. 9 is a cross-sectional view and FIG. 10 is a partial cut-away view in perspective.

FIGS. 9 and 10 illustrate an exemplary transfer element 900 including a transfer piston cup 950 inserted in mixing well 254. In the pictured embodiment, threads 956 of piston cup 950 engage threads 256 of base 250. As transfer piston cup 950 is screwed onto base 250, floor 958 of transfer piston cup 950 is forced downwards and towards floor 258 of mixing well 252. This action applies downward pressure on wiping element 260. The downward pressure causes engagement arms 262 to be released from groove 264. Once engagement arms 262 are released, wiping element 260 is free to travel downwards towards floor 258 of mixing well 252. Optionally, wiping element 260 also serves also as a piston which pushes the mixture into injection reservoir 910.

In the pictured embodiment transfer piston cup 950 is fitted with a second set of threads 952 which engage matching threads 930 on injection reservoir 910. In operation injection reservoir 910 is attached to transfer piston cup 950 by threads 930 and 952 before transfer piston cup 950 is inserted into mixing well 252. As transfer piston cup 950 descends into mixing well 252, contents of mixing well 252 (e.g. high viscosity bone cement) are forced upwards into injection reservoir 910. Injection nozzle 920 serves to release air from injection reservoir 910 so that no resistive pressure accumulates. The mixed material has been transferred 160 to the injector at this stage. Optionally, an operator of the apparatus knows that reservoir 910 is full when bone cement exits injection nozzle 920.

Exemplary Dimensions

According to various exemplary embodiments of the invention, an inner volume of the mixing well 252 is 5, optionally 10, optionally 20, optionally 40, optionally 60, optionally 80, optionally 100 ml or lesser or greater or intermediate volumes. In an exemplary embodiment of the invention, the mixing well volume is 50 to 60 ml, optionally about 66 ml, and 10 to 20 ml of mixture, optionally about 15 ml of mixture is placed in the chamber for mixing. In an exemplary embodiment of the invention, a portion of the inner volume of well 252 is occupied by mixing elements 230 and 240.

Optionally, an inner diameter of the mixing well is 20, optionally 40, optionally 60, optionally 80, optionally 100 mm or lesser or greater or intermediate sizes. In an exemplary embodiment of the invention, the inner diameter of the mixing well is 40 to 50 mm, optionally about 46 mm.

Optionally, a height of the mixing well is 20, although it can be 40, 60, 80, or 100 mm or lesser or greater or intermediate sizes. In an exemplary embodiment of the invention, the height of the mixing well is 35 to 45 mm, optionally about 40 mm.

Optionally, an aspect ratio (diameter/height) of the mixing well is 0.7, 0.9, 1.1, or 1.3, or lesser or greater or intermediate values. In an exemplary embodiment of the invention, aspect ratio (diameter/height) of the mixing well is 1.1 to 1.2, optionally about 1.15.

In an exemplary embodiment of the invention, a distance ($d_1$) between the central mixing element and the planetary mixing element (indicated by A to B in FIG. 4B) and/or a distance ($d_2$) between the planetary mixing element and an inner wall of the mixing well (indicated by C to D in FIG. 4B) is 1, 2, 3, 4, or 5 mm or lesser or greater or intermediate distances. In an exemplary embodiment of the invention, $d_1$ is substantially equivalent to $d_2$.

In typical vertebrae treatment procedures, a volume of approximately 5 ml is injected in a single vertebra. It is common to prepare a batch of approximately 8 ml of cement if a single vertebra is to be injected, approximately 15 ml of cement if two vertebrae are to be injected and progressively larger volumes if three or more vertebrae are to be injected. Combination of powdered polymer component and liquid monomer component leads to a reduction in total mixture volume as the polymer is wetted by the monomer. For example, 40 to 50 ml of polymer powder may be mixed 112 with 7 to 9 ml of monomer liquid to produce 18 ml of polymerized cement. In an exemplary embodiment of the invention, a volume of well 252 is selected to accommodate the large initial column of monomer powder, even when a significantly smaller batch of cement is being prepared.

In an exemplary embodiment of the invention, a dead volume of cement remaining in well 242 after transfer to injection reservoir 910 by transfer element 900 is less than 2, 1, or 0.5 ml or lesser or intermediate values.

In an exemplary embodiment of the invention, a diameter of central mixing element 230 and a diameter of injection reservoir 910 are both equivalent to a diameter of an aperture in wiping element 260. Optionally, this conformity of diameters reduces a dead volume of cement left in well 252 after operation of transfer apparatus 900. Optionally the diameters are all approximately 18 mm.

In other embodiments of the invention (not shown), mixing well 252 of base 250 is transferred to an injection apparatus and cement is injected into a subject directly from well 252. Optionally, this occurs after removal of mixing elements 230 and 240.

Exemplary Materials

In an exemplary embodiment of the invention, component parts of the mixing apparatus are constructed of Polyamides (e.g., Nylon) and/or Polypropylene.

Optionally, some portions of the apparatus are constructed of a metal, for example stainless steel. In an exemplary embodiment of the invention, metal is employed to construct parts which are subject to large forces, such as friction or torque. Optionally, one or more of handle 210, gears (e.g. 270), teeth (e.g. 254), drive arms (e.g. 232) and mixing elements (e.g. 230 and/or 240) are constructed of metal.

Exemplary Methods of Use

In an exemplary embodiment of the invention, apparatus 200 is provided with instructions for use. In an exemplary embodiment of the invention, the instructions indicate a procedure for achieving complete mixing of a mixture placed in well 252.

Optionally, these instructions indicate an amount of time recommended to insure complete mixing. In an exemplary embodiment of the invention, the time is 30 to 90 seconds, optionally 30 to 60 seconds, optionally about 45 seconds or lesser or greater or intermediate amounts of time.

Optionally, these instructions indicate a number of turns recommended to insure complete mixing. In an exemplary embodiment of the invention, the number of turns is 20 to 100, optionally 40 to 60, optionally about 50 or a lesser or greater or intermediate number.

Optionally, these instructions indicate a signal which will be presented to the user when mixing is complete. The signal may be a visual signal (e.g. indicator light) or an audible signal (e.g. buzzer or bell) or a tactile signal (e.g. gear 270 slips on teeth 254 when a desired viscosity is reached). In an exemplary embodiment of the invention, the signal is triggered by a closed feedback loop. The loop may rely upon, for example, an indirect measure of viscosity (e.g. torque), centripetal force, time, number of revolutions of a portion of apparatus 200 (e.g. handle 210, gear 270 or mixing element 230 and/or 240) or mixture volume.

Optionally, the apparatus combines a mechanism that allow turning of handle only during a preset window of time and/or number of rotations.

Shear Force Considerations

Shear force on a mixture within well 252 is affected primarily by surface properties, distance between surfaces, and differences in velocities between surfaces.

Surface properties of mixing elements 230, 240 and an inner surface of well 252 all affect applied shear forces on mixture 500 (FIG. 5). Increasing roughness (e.g. by serration or striation) prevents mixture 500 from slipping against these surfaces by increasing the force of friction. When the surfaces are sufficiently roughened, a boundary layer will have a relative velocity of zero with respect to the surface. Optionally, this zero relative velocity contributes to increased shear force.

Distances between surfaces are inversely related to shear forces acting on a mixture 500 moving between the surfaces. In an exemplary embodiment of the invention, as distances defined by lines A-B and/or C-D (FIG. 4B) increase, an applied shear force to a portion of mixture 500 crossing those lines decreases.

Differences in relative velocities between portions of mixer 200 also affect shear forces on mixture 200. As the difference in relative velocities increases, the applied shear force to a portion of mixture 500 flowing between the elements increases. The relative velocities are optionally influenced by angular velocities and/or radial velocities and/or radius of the elements involved as discussed in more detail above. In an exemplary embodiment of the invention, differences in relative velocity are amplified by imparting angular velocities with different directions to mixing elements 240 and 230.

General

Because some components of a bone cement mixture may have an unpleasant odor and/or be toxic if inhaled, some exemplary embodiments of the invention include safety features to reduce exposure to undesired vapors.

In an exemplary embodiment of the invention, locking ring 224 is equipped with an air-tight seal (e.g. rubber or silicon) which prevents vapors from escaping from well 252.

Alternatively or additionally, apparatus 200 may be provided with an evacuation port (not shown) connectable to a vacuum source. In an exemplary embodiment of the invention, the vacuum source is a standard "wall suction" unit in a hospital operating room and the undesired vapors are from an MMA component of a bone cement mixture.

In cases where apparatus 200 is supplied with components to be mixed inside well 252, a method for preventing undesired premature mixing may be implemented.

One exemplary method of preventing undesired premature mixing of monomer liquid and polymer powder is to provide the monomer liquid in a sealed bag or capsule which is burst when apparatus 200 is operated. The capsule may be burst when it is drawn across line A-B or C-D by the flow of mixture 500. In an exemplary embodiment of the invention, the capsule is designed so that it is characterized by a smallest dimension which exceeds the length of A-B and/or C-D. In an exemplary embodiment of the invention, the bag or capsule is constructed of a biocompatible material which may be injected together with the bone cement.

Another exemplary method of preventing undesired premature mixing of monomer liquid and polymer powder is to provide the monomer liquid inside central mixing element 230. Optionally, partial removal of cover 220 from base 250 permits the monomer liquid to exit mixing element 230 into well 252. Optionally, tightening of locking ring 224 breaks a seal in mixing element 230. Breaking the seal releases the liquid monomer onto the powder component.

Another exemplary method of preventing undesired premature mixing of monomer liquid and polymer powder is to provide the monomer liquid in a cavity inside a wall of mixing well 252. Optionally, contents of the cavity are dumped into well 252 manually or automatically when mixing commences.

The present invention has been described using detailed descriptions of embodiments thereof that are provided by way of example and are not intended to necessarily limit the scope of the invention. In particular, numerical values may be higher or lower than ranges of numbers set forth above and still be within the scope of the invention. The described embodiments comprise different features, not all of which are required in all embodiments of the invention. Some embodiments of the invention utilize only some of the features or possible combinations of the features. Alternatively or additionally, portions of the invention described/depicted as a single unit may reside in two or more separate physical entities which act in concert to perform the described/depicted function. Alternatively or additionally, portions of the invention described/depicted as two or more separate physical entities may be integrated into a single physical entity to perform the described/depicted function. Variations of embodiments of the present invention that are described and embodiments of the present invention comprising different combinations of features noted in the described embodiments can be combined in all possible combinations including, but not limited to use of features described in the context of one embodiment in the context of any other embodiment. The scope of the invention is limited only by the following claims.

In the description and claims of the present application, each of the verbs "comprise", "include" and "have" as well as any conjugates thereof, are used to indicate that the object or objects of the verb are not necessarily a complete listing of members, components, elements or parts of the subject or subjects of the verb.

All publications and/or patents and/or product descriptions cited in this document are fully incorporated herein by reference to the same extent as if each had been individually incorporated herein by reference.

The invention claimed is:

1. A mixing apparatus, the apparatus comprising:
   a) a mixing well characterized by an internal volume not exceeding 100 ml.;
   b) a drive mechanism including a stationary circumferential gear on an inner surface of the mixing well;
   c) a planetary mixing element driven by a mixing element gear which engages the stationary circumferential gear;
   d) a central mixing element positioned substantially at a center of the mixing well; and
   e) a wiping element adapted to concurrently engage an inner surface of the mixing well and the planetary mixing element
   wherein the planetary mixing element revolves around the central mixing element.

2. Apparatus according to claim 1, wherein the drive mechanism is adapted to provide sufficient shear force to mix a mixture characterized by a viscosity of at least 500 Pascal/second.

3. Apparatus according to claim 2, wherein the viscosity of at least 500 Pascal/second is achieved within 90 seconds of an onset of mixing.

4. Apparatus according to claim 1, comprising:
   f) a cover engageable by the mixing well and adapted for closure thereof.

5. Apparatus according to claim 4, wherein the cover includes a locking ring.

6. Apparatus according to claim 1, wherein the drive mechanism is adapted for manual operation.

7. Apparatus according to claim 1
   wherein the wiping element is adapted to concurrently engage an inner surface of the mixing well and the planetary mixing element.

8. Apparatus according to claim 1, comprising:
   e) a wiping element adapted to concurrently engage an inner surface of the mixing well, the planetary mixing element and the central mixing element.

9. Apparatus according to claim 1, wherein the central mixing element rotates about its own axis.

10. Apparatus according to claim 9, wherein the central mixing element and the planetary mixing element rotate in opposite directions.

11. A mixing apparatus, the apparatus comprising:
   a) a mixing well characterized by an internal volume not exceeding 100 ml.;
   b) a central mixing element deployed substantially at a center of the mixing well;
   c) at least one planetary mixing element which revolves around the central mixing element;
   wherein a first distance ($d_1$) between the central mixing element and the planetary mixing element is substantially equivalent to a second distance ($d_2$) between the planetary mixing element and an inner surface of the mixing well.

12. Apparatus according to claim 11, wherein the planetary mixing element is adapted for manual operation.

13. Apparatus according to claim 10, wherein the planetary mixing element and central mixing element are adapted to provide sufficient shear force to mix a mixture characterized by a viscosity of at least 500 Pascal/second.

14. A method of mixing components of a viscous mixture, the method comprising:
   a) placing the components in a mixing well characterized by an inner volume of not more than 100 ml;
   b) deploying a drive mechanism including a stationary circumferential gear on an inner surface of the mixing well, at least one planetary mixing element driven by a mixing element gear which engages the stationary circumferential gear, and a central mixing element in the mixing well; and
   c) operating the drive mechanism to cause the planetary mixing element to both rotate about its own axis and revolve around the central mixing element in order to mix the components to form a mixture;
   wherein the drive mechanism is adapted to provide sufficient shear force to mix a mixture characterized by a viscosity of at least 500 Pascal/second.

15. A method according to claim 14, comprising:
   d) engaging a wiping element to at least one of the mixing elements such that withdrawal of the mixing element from the mixing well causes the wiping element to wipe mixture from the mixing element.

16. A method according to claim 14, wherein the viscosity of at least 500 Pascal/second is achieved within 90 seconds of an onset of mixing.

17. A method according to claim 14, wherein the drive mechanism is a manual drive mechanism and the method comprises manually operating the drive mechanism.

18. A method according to claim 17, wherein the drive mechanism is adapted to provide sufficient shear force to mix a mixture characterized by a viscosity of at least 500 Pascal/second.

19. A method of mixing components of a viscous mixture, the method comprising:
   a) placing the components in a mixing well characterized by an inner volume of not more than 100 ml;
   b) deploying a drive mechanism including a stationary circumferential gear on an inner surface of the mixing well, at least one planetary mixing element driven by a mixing element gear which engages the stationary circumferential gear, and a central mixing element in the mixing well; and
   c) operating the drive mechanism to cause the planetary mixing element to both rotate about its own axis and revolve around the central mixing element in order to mix the components to form a mixture;
   wherein the drive mechanism is a manual drive mechanism and the method comprises manually operating the drive mechanism.

20. A method according to claim 19, comprising:
   d) engaging a wiping element to at least one of the mixing elements such that withdrawal of the mixing element from the mixing well causes the wiping element to wipe mixture from the mixing element.

21. A method according to claim 19, wherein the manual drive mechanism supplies a sufficient force to cause the planetary mixing element to move through a mixture characterized by a viscosity of at least 500 Pascal-second.

22. A method according to claim 21, wherein the viscosity of at least 500 Pascal/second is achieved within 90 seconds of an onset of mixing.

* * * * *

UNITED STATES PATENT AND TRADEMARK OFFICE
CERTIFICATE OF CORRECTION

PATENT NO. : 8,360,629 B2
APPLICATION NO. : 11/428908
DATED : January 29, 2013
INVENTOR(S) : Oren Globerman et al.

It is certified that error appears in the above-identified patent and that said Letters Patent is hereby corrected as shown below:

In the Claims

Starting at column 15, line 11 and ending at column 16, line 22, delete the entirety of claim 7 through claim 18, and replace with the following claims 7 through 18.

7. Apparatus according to claim 1, wherein the wiping element is adapted to concurrently engage an inner surface of the mixing well, the planetary mixing element and the central mixing element.

8. Apparatus according to claim 1, wherein the central mixing element rotates about its own axis.

9. Apparatus according to claim 8, wherein the central mixing element and the planetary mixing element rotate in opposite directions.

10. A mixing apparatus, the apparatus comprising:
   a) a mixing well characterized by an internal volume not exceeding 100 ml.;
   b) a central mixing element deployed substantially at a center of the mixing well;
   c) at least one planetary mixing element which revolves around the central mixing element;
wherein a first distance (d1) between the central mixing element and the planetary mixing element is substantially equivalent to a second distance (d2) between the planetary mixing element and an inner surface of the mixing well.

11. Apparatus according to claim 10, wherein the planetary mixing element is adapted for manual operation.

12. Apparatus according to claim 9, wherein the planetary mixing element and central mixing element are adapted to provide sufficient shear force to mix a mixture characterized by a viscosity of at least 500 Pascal/second.

Signed and Sealed this
Sixteenth Day of July, 2013

Teresa Stanek Rea
*Acting Director of the United States Patent and Trademark Office*

13. A method of mixing components of a viscous mixture, the method comprising:
   a) placing the components in a mixing well characterized by an inner volume of not more than 100 ml;
   b) deploying a drive mechanism including a stationary circumferential gear on an inner surface of the mixing well, at least one planetary mixing element driven by a mixing element gear which engages the stationary circumferential gear, and a central mixing element in the mixing well; and
   c) operating the drive mechanism to cause the planetary mixing element to both rotate about its own axis and revolve around the central mixing element in order to mix the components to form a mixture;
   wherein the drive mechanism is adapted to provide sufficient shear force to mix a mixture characterized by a viscosity of at least 500 Pascal/second.

14. A method according to claim 13, comprising:
   d) engaging a wiping element to at least one of the mixing elements such that withdrawal of the mixing element from the mixing well causes the wiping element to wipe mixture from the mixing element.

15. A method according to claim 13, wherein the viscosity of at least 500 Pascal/second is achieved within 90 seconds of an onset of mixing.

16. A method according to claim 13, wherein the drive mechanism is a manual drive mechanism and the method comprises manually operating the drive mechanism.

17. A method according to claim 16, wherein the manual drive mechanism supplies a sufficient force to cause the planetary mixing element to move through a mixture characterized by a viscosity of at least 500 Pascal-second.

18. An apparatus according to claim 10, wherein the mixing elements are substantially cylindrical.